United States Patent
Gonzalez et al.

(10) Patent No.: US 6,335,157 B1
(45) Date of Patent: Jan. 1, 2002

(54) METHOD BASED ON LOCALIZATION OF HSP90 TO THE CENTROSOME

(75) Inventors: Cayetano Gonzalez; Bodo Lange, both of Heidelberg (DE)

(73) Assignee: The European Molecular Biology Laboratory, Heidelberg (DE)

(*) Notice: Subject to any disclaimer, the term of this patent is extended or adjusted under 35 U.S.C. 154(b) by 0 days.

(21) Appl. No.: 09/307,143

(22) Filed: May 7, 1999

(51) Int. Cl.⁷ .......................... C12Q 1/00; G01N 33/53; C12P 21/06; B01D 59/44
(52) U.S. Cl. ............................. 435/4; 435/7.1; 435/7.2; 435/7.4; 435/7.94; 435/69.1; 250/281
(58) Field of Search .............................. 435/4, 7.1, 7.4, 435/7.2, 7.94, 69.1; 250/281

(56) References Cited

FOREIGN PATENT DOCUMENTS

| FR | 2688227 A | 9/1993 |
|----|-----------|--------|
| WO | WO 00/08135 | 2/2000 |

OTHER PUBLICATIONS

Liang et al., 1997, Molecular chaperones and the cytoskeleton, J. Cell Science 110(13):1431–1440.
Uzawa et al., 1995, Identification of a complex between centrin and heat shock proteins in CSF–arrested *Xenopus oocytes* and dissociation of the complex folowing oocyte activation, Developmental Biology 171(1):51–59.
Simizu et al., 2000, Mutations in the Plk gene lead to instability of Plk protein in human tumor cell lines, Nature Cell Biology 2:852–854.
de Cácer et al., Requirement of Hsp90 for centrosomal function reflects its regulation of Polo kinase stability, manuscript in preparation.
Stebbins et al., 1997, Crystal Structure of an Hsp90–Geldanamycin Complex: Targeting of a Protein Chaparone by an Antitumor Agent, Cell 89:239–250.
Supko et al., 1995, Preclinical pharmacologic evaluation of geldanamycin as an antitumor agent, Cancer Chemother Pharmacol 36:305–315.
Schrijvers and Vermorken, 2000, Role of Taxoids in Head and Neck Cancer, The Oncologist 5:199–208.
www.ncbi.nlm.nih.gov (National Center for Biotechnology Information) Genbank Accession No. JC2343 Heat shock protein 90 alpha—zebra fish. Database [Online]. Last update: Nov. 15, 1996. Accessed on: May 6, 1999.
Bohen and Yahamoto, 1994, "Modulation of steroid receptor signal transduction by heat shock proteins" in The Biology of Heat Shock Proteins and Molecular Chaperones (Cold Spring Harbor Laboratory Press) pp. 313–334.
Borkovich et al., 1989, "Hsp82 is an essential protein that is required in higher concentrations for growth of cells at higher temperatures", Mol Cell Biol. 1989 9:3919–30.

Bornens and Moudjou, 1999, "Studying the composition and function of centrosomes in vertebrates", Methods Cell Biol. 61:13–34.
Brown et al., 1996, "Molecular chaperones and the centrosome", J. Biol. Chem. 271:824–832.
Buchner, 1999, "Hsp90 & Co.—a holding for folding", TIBS 24:136–141.
Caplan, 1999, "Hsp90's secrets unfold: new insights from structural and functional studies", Trends Cell Biol. 9:262–268.
Catelli et al., 1985, "The common 90–kd protein component of non–transformed '8S' steroid receptors is a heat–shock protein", EMBO J. 4:3131–5.
Csermely et al., 1998, "The 90–kDa molecular chaperone family: structure, function, and clinical applications. A comprehensive review", Pharmacol. Ther. 79:129–168.
Cutforth and Rubin, 1994, "Mutations in Hsp83 and cdc37 impair signaling by the sevenless receptor tyrosine Cannaceae in Drosophila", Cell 77:1027–36.
Doxsey, 1998, "The centrosome—a tiny organelle with big potential", Nature Gen. 20:104–107.
Fabunmi et al., 2000, "Activity and regulation of the centrosome–associated proteasome", J. Biol. Chem. 275:409–413.
Hartson et al., 1999, "Molybdate inhibits Hsp90, induces structural changes in its C–terminus domain, and alters its interactions with substrates", Biochem 38:3837–3849.
Kalt and Schliwa, 1993, "Molecular components of the centrosome", Trends Cell Biol. 3:118–128.
Krone et al., 1994, "HEP 90 alpha and HSP 90 beta genes are present in the zebrafish and are differentially regulated in developing embryos", Biochem Biophys Res Commun. 204:746–52.
Miyata and Yahara, 1992, "The 90–kDa heat shock protein, HSP90, binds and protects casein kinase II from self–aggregation and enhances its kinase activity", J Biol Chem. 267:7042–7.

(List continued on next page.)

Primary Examiner—Anthony C. Caputa
Assistant Examiner—Gary B. Nickol
(74) Attorney, Agent, or Firm—Pennie & Edmonds LLP

(57) ABSTRACT

The present invention is directed to methods for screening for fragments, derivatives and analogs of Hsp90 that are altered in their subcellular localization, and thus, altered in their activity as compared to wild type Hsp90. The present invention is also directed to screening for modulators of Hsp90 activity as determined by assaying for altered subcellular localization of Hsp90. The present invention is further directed to diagnostic, prognostic and screening uses of Hsp90/centrosome co-purification.

18 Claims, 17 Drawing Sheets

OTHER PUBLICATIONS

Figure 4:
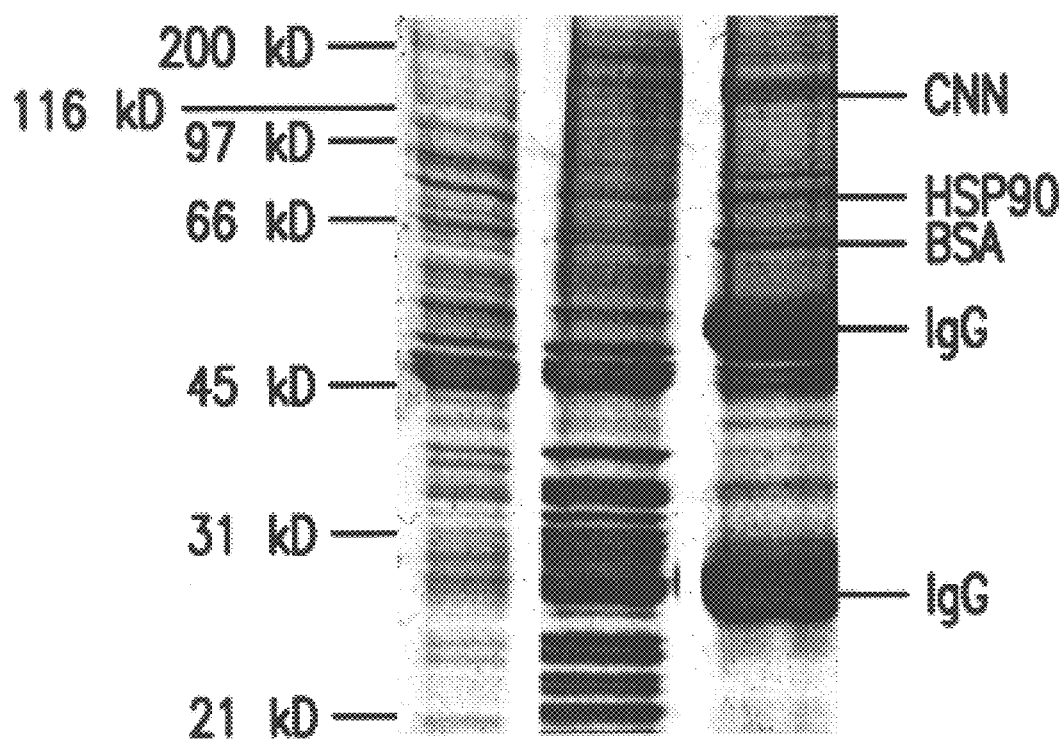

Nathan and Lindquist, 1995, "Mutational analysis of hsp90 function: interactions with a steroid receptor and a protein kinase", Mol. Cell. Biol. 15:3917–3925.

Nathan et al., 1997, "In vivo functions of the *Saccharomyces cerevisiae* Hsp90 chaperone", Proc. Natl. Acad. Sci. 94:12949–12956.

Neubauer et al., 1997, "Identification of the proteins of the yeast U1 small nuclear ribonucleoprotein complex by mass spectrometry", Proc Natl Acad Sci U S A. 94:385–90.

Neubauer et al., 1998, "Mass spectrometry and EST–database searching allows characterization of the multi–protein spliceosome complex", Nat Genet. 20:46–50.

Parsell et al., 1993, "The function of heat–shock proteins in stress tolerance: degradation and reactivation of damaged proteins", Annu Rev Genet. 27:437–96.

Pratt and Toft, 1997, "Steroid receptor interactions with heat shock protein and immunophilin chaperones", Endocrin Rev. 18:306–360.

Pratt, 1997, "The role of the hsp90–based chaperone system in signal transduction by nuclear receptors and receptors signaling via MAP kinase", Annu Rev Pharmacol Toxicol. 37:297–326.

Scheibel and Buchner, 1998, "The Hsp90 complex—a super–chaperone machine as a novel drug target", Biochem Pharmacol. 56:675–82.

Scheibel and Buchner, 1997, "The Hsp90 Family—An Overview" in Guidebook to Molecular Chaperones and Protein Catalysts (Oxford University Press) pp. 147–151.

Stancato et al., 1993, "Raf exists in a native heterocomplex with hsp90 and p50 that can be reconstituted in a cell–free system", J Biol Chem. 268:21711–6.

van der Straten et al., 1997, "The heat shock protein 83 (Hsp83) is required for Raf–mediated signalling in Drosophila", EMBO J. 16:1961–9.

Wartmann et al., 1994, "The native structure of the activated Raf protein kinase is a membrane–bound multi–subunit complex", J Biol Chem. 269:6695–701.

Wigley et al., 1999, "Dynamic association of proteasomal machinery with the centrosome", J. Cell Biol. 145:481–490.

Wilm et al., 1996, "Femtomole sequencing of proteins from polyacrylamide gels by nano–electrospray mass spectrometry", Nature. 379:466–9.

Xu and Lindquist, 1993, "Heat–shock protein hsp90 governs the activity of pp60v–src kinase", Proc Natl Acad Sci U S A. 90:7074–8.

Zarzov et al., 1997, "A yeast heat shock transcription factor (Hsf1) mutant is defective in both Hsc82/Hsp82 synthesis and spindle poly body duplication", J. Cell Science 110:1879–1891.

Zimmerman et al., "Amorphous no longer: the centrosome comes into focus", Curr. Opin. Cell Biol. 11:122–128, 1999.

www.ncbi.nlm.nih.gov (National Center for Biotechnology Information) Genbank Accession No. 1093612. heat shock protein 90. Database [Online]. Last update: Jul. 10, 1992. Accessed on: May 6, 1999.

www.ncbi.nlm.nih.gov (National Center for Biotechnology Information) Genbank Accession No. AAA31439. hsp90 binding protein. Database [Online]. Last update: Jul. 14, 1992. Accessed on: May 6, 1999.

www.ncbi.nlm.nih.gov (National Center for Biotechnology Information) Genbank Accession No. CAA30251 Heat shock protein 90 (AA 1–728). Database [Online]. Last update: Sep. 12, 1993, Accessed on: May 6, 1999.

www.ncbi.nlm.nih.gov (National Center for Biotechnology Information) Genbank Accession No. M16660 Human 90–kDa heat–shock protein gene, cDNA, complete cds. Database [Online]. Last update: Jun. 11, 1993. Accessed on: May 6, 1999.

www.ncbi.nlm.nih.gov (National Center for Biotechnology Information) Genbank Accession No. P34058 Heat shock protein hsp 90–beta (hsp 84). Database [Online]. Last update: Dec. 15, 1998. Accessed on: May 6, 1999.

www.ncbi.nlm.nih.gov (National Center for Biotechnology Information) Genbank Accession No. P27890 Heat shock protein 90 (hsp 90). Database [Online]. Last update: Oct. 1, 1993. Accessed on: May 6, 1999.

www.ncbi.nlm.nih.gov (National Center for Biotechnology Information) Genbank Accession No. P46633 Heat shock protein hsp 90–alpha (hsp 86). Database [Online]. Last update: Oct. 1, 1996. Accessed on: May 6, 1999.

www.ncbi.nlm.nih.gov (National Center for Biotechnology Information) Genbank Accession No. Q04619 Heat shock cognate protein hsp 90–beta. Database [Online]. Last update: Oct. 1, 1996. Accessed on: May 6, 1999.

www.ncbi.nlm.nih.gov (National Center for Biotechnology Information) Genbank Accession No. X03810 *Drosophila melanogaster* gene for heat shock protein hsp 82. Database [Online]. Last update: Nov. 7, 1997. Accessed on: May 6, 1999.

www.ncbi.nlm.nih.gov (National Center for Biotechnology Information) Genbank Accession No. X15183 Human mRNA for 90kDa heat–shock protein. Database [Online]. Last update: Jan. 30, 1995. Accessed on: May 6, 1999.

| | | | | | |
|---|---|---|---|---|---|
|GGATCCTTAA|CCGGGAACTT|GAAGAAGTGC|ATATTGGGGT|TGCGGCTAGA|ACCCACCGGA  60|
|CAATCACGAA|AACAACACTT|AGTGCCGCCC|ATTTGTTTAA|ATATAAGCAA|ACAACTTTTA 120|
|TGTTATTAGT|GGTGGAAGTG|TTAGCGTCAG|CTGGTGATAT|CGATGGGAGG|CATCGATAAC 180|
|AGAATTGACC|GAAACCAAAT|GATCGATATG|ACACTTCTTA|ATTAATGAGA|GATTTTTTAC 240|
|TTGACTGGGC|ATGTAGCAGG|TTTTGCACAG|AAGCAATTAT|TTTCCGGAAT|GTGAAATGTC 300|
|TGCTTTTTAG|CTAATTACAA|CAAAAACTTT|CCAATTTTTG|TTCCCCAAAC|CCACTCAAGT 360|
|GATTTCAAAT|TTTACCGTCC|GCTTAAAATG|GAACTAGTTC|CAGAGGAACC|AGCTTGCACC 420|
|ACCAAGTCTC|TGAAACTCTG|GAAATATCGA|TAGTCTGGTG|GAGAAAAGTA|TTCATAAATA 480|
|TAAATAAAAA|TTAACAGGTC|ATAAGCTGAT|TTGTTTATTA|TTTACTGTTA|AAACAAGTAA 540|
|AATAATATTG|GGAACAATTA|AATTTTCCAT|TTTCCTAATT|ACAGTATAAG|CCTAGTGGGC 600|
|GTTTTGATAT|CCAATTGTAA|TGTTTTAAGC|AATCCCAGTG|GGCTTTGCTC|AATCGTTCGG 660|
|ACCACTTAGA|CGAATTTCCA|CCAAACTTAG|TTCAGTATAA|TTTTTGAATT|CGCCCGCACA 720|
|GGTTGCGCAC|TTTTCGACCG|TATCACAACA|CTGATCTACC|CTAGTATTCA|CAGGAAGTTG 780|
|CATCCCTGGC|ATCCAGAAGC|CTCTAGAAGT|TTCTAGAGAC|TTCCAGTTCG|GGTCGGGTTT 840|
|TTCTATAAAA|GCAGACGCGC|GGCGTTTGCC|GGTTCGAGTC|TTGAAAAAAA|TTTCGTACGG 900|
|TGTGCGTCGT|AACAACAAGC|AGCGTCTGAA|AAGTTTTGTG|AATTTCCAAT|TCTATACAAA 960|
|GCAAAGTGAA|AATATCTGTA|TTTTTACCTT|TATTCTGTGA|ATAGAACGAA|AAACATACAT 1020|
|ACAAGGTGAG|TAATGCAAAT|TAAAAGAAAA|GAGTGAATAG|TTTCAGTGGC|TATGGCCAAA 1080|
|ATGTGCATTT|TGCGTGGTCC|TGTGCATCTC|GAATGTTCTT|GACCCAAATG|TGAGATATTG 1140|
|ATTTTAAATT|TCTAGGAGCC|AAGTTTAAGA|ATTTTTTTTA|TTTAATTAGA|GGTGGCAACG 1200|
|TGCAAATTAA|CTCAAAATTC|CGGTTTCTTT|TATTTTTTGT|CGCTTGGACG|CATCTTCCAG 1260|
|AGGTTTCTAT|GCTTTAGCAT|GAATTAAACA|TCGTGCCAAA|TAGGCCTTTT|AATTATATAT 1320|
|TACTGTCCTT|TATTTACAAT|TACATGTGGT|TTCTAGAATA|CAAGATTAAT|TTTTGTTTAA 1380|
|TTAATGCAAT|GGTCTTTTAG|CGCTAAATCG|AATTATGCCG|CTCTTTTTAG|GGGTGACAAT 1440|
|GCGCAAATCA|CATTTGCCGC|TCGAGAATGT|TCTAGAGGTT|TCTATGCTTT|AGCATGAATT 1500|
|AAACAGCGTG|CCAAATAGGC|TTTTTAATTA|TAAATTACTG|TCCTTCATTT|ACATTTACAC 1560|
|GTGCTTTCTT|TGCATTCCCA|TTTTAAATTG|CACATGCCGC|ATACGCACAT|GCACGCCCAT 1620|
|GACTAATACT|TTCAAGTAAA|AATGTGGCGT|CAGTAAGCAA|ATTCTGTTAA|ATCGGTTTTT 1680|
|TAATCCTATT|TGCTCTATTT|TAATTGGTTG|GTTGCTACTA|GCAACTTGCT|AGGCGAATTA 1740|
|GTTTTCCTTT|GGCTTCTAGA|TGCTTCCACA|AACTTCCTTG|GTGAAGTACG|AATTTTCAAT 1800|
|GCAATGCTCA|CTCACACAGA|CACGAGTTTG|CACACAGCAG|GGGTAGAAAA|ATTATCAACC 1860|
|GACCCAATTT|GCATAATTAT|ATTTAAATAT|TTAAATTTAA|AACATTATTT|TGCAACTTAA 1920|
|AATCAATTCT|GTTGCCTAAT|TGAAATTAAA|ATTCCATTTT|ACGGGTTGCA|AAGTGAATGC 1980|
|TATAATTTTG|ACCACCACTG|TACTTGTATA|TGCGCATGTT|AAATGAGGCA|TGTGCAAAAG 2040|
|AGAAAGAAAG|AAAAAGAATA|AAACCGGAGC|AGCTGCTGAA|AATGCAGCTG|CTTTTCCTTA 2100|
|GTGTTGAACC|CACAGACTAT|AACTAATCCT|AATGATTTTG|TAAATCCATT|GCAG ATG 2157|
| | | | | |Met|
| | | | | |1|

| | | | | | |
|---|---|---|---|---|---|---|
|CCA|GAA GAA|GCA GAG|ACC TTT|GCA TTC|CAG GCT GAG ATT GCT CAG CTG 2205|
|Pro|Glu Glu|Ala Glu|Thr Phe|Ala Phe|Gln Ala Glu Ile Ala Gln Leu|
| |5| |10| |15|

FIG.1A

```
ATG TCC CTG ATC ATC AAC ACA TTC TAC TCG AAC AAG GAG ATT TTC CTG    2253
Met Ser Leu Ile Ile Asn Thr Phe Tyr Ser Asn Lys Glu Ile Phe Leu
        20              25              30

CGC GAG TTG ATC TCG AAC GCT TCC GAT GCC CTG GAC AAG ATC CGC TAT    2301
Arg Glu Leu Ile Ser Asn Ala Ser Asp Ala Leu Asp Lys Ile Arg Tyr
        35              40              45

GAG TCC CTT ACT GAC CCC AGC AAG CTG GAC TCT GGC AAG GAG CTG TAC    2349
Glu Ser Leu Thr Asp Pro Ser Lys Leu Asp Ser Gly Lys Glu Leu Tyr
50              55              60              65

ATC AAG CTG ATC CCT AAC AAG ACG GCT GGT ACT CTG ACC ATC ATT GAT    2397
Ile Lys Leu Ile Pro Asn Lys Thr Ala Gly Thr Leu Thr Ile Ile Asp
                70              75              80

ACC GGT ATC GGT ATG ACC AAG TCC GAC CTG GTC AAC AAC TTG GGA ACC    2445
Thr Gly Ile Gly Met Thr Lys Ser Asp Leu Val Asn Asn Leu Gly Thr
            85              90              95

ATC GCC AAG TCC GGA ACC AAG GCC TTC ATG GAG GCT CTG CAG GCT GGT    2493
Ile Ala Lys Ser Gly Thr Lys Ala Phe Met Glu Ala Leu Gln Ala Gly
            100             105             110

GCC GAC ATT TCC ATG ATC GGT CAG TTC GGT GTG GGT TTC TAC TCC GCC    2541
Ala Asp Ile Ser Met Ile Gly Gln Phe Gly Val Gly Phe Tyr Ser Ala
        115             120             125

TAC CTG GTC GCC GAC AAG GTG ACT GTC ACC TCC AAG AAC AAC GAT GAC    2589
Tyr Leu Val Ala Asp Lys Val Thr Val Thr Ser Lys Asn Asn Asp Asp
130             135             140             145

GAG CAG TAC GTG TGG GAG TCC TCT GCC GGA GGC TCT TTC ACA GTC CGT    2637
Glu Gln Tyr Val Trp Glu Ser Ser Ala Gly Gly Ser Phe Thr Val Arg
                150             155             160

GCC GAC AAC TCT GAG CCC CTG GGC CGT GGC ACC AAG ATC GTG CTG TAC    2685
Ala Asp Asn Ser Glu Pro Leu Gly Arg Gly Thr Lys Ile Val Leu Tyr
                165             170             175

ATC AAG GAG GAC CAG ACC GAC TAT CTG GAG GAG AGC AAG ATC AAG GAG    2733
Ile Lys Glu Asp Gln Thr Asp Tyr Leu Glu Glu Ser Lys Ile Lys Glu
            180             185             190
```

FIG.1B

```
ATT GTT AAC AAG CAC TCC CAG TTC ATT GGC TAC CCC ATC AAG CTG CTC     2781
Ile Val Asn Lys His Ser Gln Phe Ile Gly Tyr Pro Ile Lys Leu Leu
    195             200                 205

GTA GAG AAG GAG CGC GAG AAG GAG GTC AGC GAC GAT GAG GCT GAT GAT     2829
Val Glu Lys Glu Arg Glu Lys Glu Val Ser Asp Asp Glu Ala Asp Asp
210             215                 220                 225

GAG AAG AAG GAA GGT GAT GAG AAG AAG GAG ATG GAG ACT GAT GAG CCC     2877
Glu Lys Lys Glu Gly Asp Glu Lys Lys Glu Met Glu Thr Asp Glu Pro
                230                 235                 240

AAA ATC GAG GAT GTT GGC GAG GAT GAG GAT GCC GAC AAG AAG GAC AAG     2925
Lys Ile Glu Asp Val Gly Glu Asp Glu Asp Ala Asp Lys Lys Asp Lys
                245                 250                 255

GAT GCC AAG AAG AAG AAG ACC ATC AAG GAG AAG TAC ACT GAG GAT GAG     2973
Asp Ala Lys Lys Lys Lys Thr Ile Lys Glu Lys Tyr Thr Glu Asp Glu
        260                 265                 270

GAG CTG AAC AAG ACC AAG CCC ATC TGG ACC CGC AAT CCC GAT GAT ATC     3021
Glu Leu Asn Lys Thr Lys Pro Ile Trp Thr Arg Asn Pro Asp Asp Ile
    275                 280                 285

TCC CAG GAG GAG TAC GGC GAG TTC TAC AAA TCC CTG ACC AAC GAC TGG     3069
Ser Gln Glu Glu Tyr Gly Glu Phe Tyr Lys Ser Leu Thr Asn Asp Trp
290             295                 300                 305

GAG GAT CAT CTG GCC GTC AAG CAC TTC TCC GTG GAG GGT CAG CTG GAG     3117
Glu Asp His Leu Ala Val Lys His Phe Ser Val Glu Gly Gln Leu Glu
                310                 315                 320

TTC CGT GCT CTG CTC TTC ATT CCC CGT CGC ACG CCC TTC GAT CTC TTT     3165
Phe Arg Ala Leu Leu Phe Ile Pro Arg Arg Thr Pro Phe Asp Leu Phe
                325                 330                 335

GAG AAC CAG AAG AAG CGC AAC AAC ATC AAG CTG TAC GTG CGT CGT GTC     3213
Glu Asn Gln Lys Lys Arg Asn Asn Ile Lys Leu Tyr Val Arg Arg Val
                340                 345                 350

TTC ATC ATG GAC AAC TGC GAG GAC CTC ATT CCA GAG TAC TTG AAC TTC     3261
Phe Ile Met Asp Asn Cys Glu Asp Leu Ile Pro Glu Tyr Leu Asn Phe
    355                 360                 365
```

FIG.1C

```
ATG AAG GGT GTG GTC GAC TCC GAG GAT CTG CCC CTC AAC ATC TCA CGT    3309
Met Lys Gly Val Val Asp Ser Glu Asp Leu Pro Leu Asn Ile Ser Arg
370             375                 380                 385

GAG ATG CTG CAG CAG AAC AAG GTC CTA AAG GTG ATC CGC AAG AAC CTG    3357
Glu Met Leu Gln Gln Asn Lys Val Leu Lys Val Ile Arg Lys Asn Leu
                390                 395                 400

GTC AAG AAG ACC ATG GAG CTG ATT GAG GAG CTC ACC GAG GAC AAG GAG    3405
Val Lys Lys Thr Met Glu Leu Ile Glu Glu Leu Thr Glu Asp Lys Glu
                405                 410                 415

AAC TAC AAG AAG TTC TAT GAC CAG TTC AGC AAG AAC CTG AAG CTG GGT    3453
Asn Tyr Lys Lys Phe Tyr Asp Gln Phe Ser Lys Asn Leu Lys Leu Gly
                420                 425                 430

GTG CAC GAG GAC AGC AAC AAC CGT GCC AAG TTG GCC GAC TTC CTT CGC    3501
Val His Glu Asp Ser Asn Asn Arg Ala Lys Leu Ala Asp Phe Leu Arg
                435                 440                 445

TTC CAC ACC TCT GCC TCC GGC GAC GAT TTC TGC TCC CTG GCC GAC TAC    3549
Phe His Thr Ser Ala Ser Gly Asp Asp Phe Cys Ser Leu Ala Asp Tyr
450                 455                 460                 465

GTG TCG CGC ATG AAG GAT AAC CAG AAG CAC GTG TAC TTC ATC ACT GGC    3597
Val Ser Arg Met Lys Asp Asn Gln Lys His Val Tyr Phe Ile Thr Gly
                470                 475                 480

GAG TCC AAG GAC CAG GTC AGC AAC TCT GCC TTC GTG GAG CGC GTC AAG    3645
Glu Ser Lys Asp Gln Val Ser Asn Ser Ala Phe Val Glu Arg Val Lys
                485                 490                 495

GCC CGT GGC TTC GAG GTG GTC TAC ATG ACC GAG CCC ATC GAT GAG TAT    3693
Ala Arg Gly Phe Glu Val Val Tyr Met Thr Glu Pro Ile Asp Glu Tyr
                500                 505                 510

GTC ATC CAG CAC TTG AAG GAG TAC AAG GGC AAG CAG CTG GTC TCT GTC    3741
Val Ile Gln His Leu Lys Glu Tyr Lys Gly Lys Gln Leu Val Ser Val
                515                 520                 525

ACC AAG GAG GGT CTG GAG CTG CCT GAG GAT GAG AGC GAG AAG AAG AAG    3789
Thr Lys Glu Gly Leu Glu Leu Pro Glu Asp Glu Ser Glu Lys Lys Lys
530                 535                 540                 545
```

FIG.1D

| | | | | | | | | | | | | | | |
|---|---|---|---|---|---|---|---|---|---|---|---|---|---|---|
| CGC | GAG | GAG | GAC | AAG | GCC | AAG | TTC | GAG | AGC | CTG | TGC | AAG | CTG | ATG | AAG | 3837
| Arg | Glu | Glu | Asp | Lys | Ala | Lys | Phe | Glu | Ser | Leu | Cys | Lys | Leu | Met | Lys |
| | | | | 550 | | | | 555 | | | | | 560 | | |

CGC GAG GAG GAC AAG GCC AAG TTC GAG AGC CTG TGC AAG CTG ATG AAG    3837
Arg Glu Glu Asp Lys Ala Lys Phe Glu Ser Leu Cys Lys Leu Met Lys
            550             555                 560

TCC ATC CTG GAC AAC AAG GTC GAG AAG GTG GTG GTG TCC AAC CGC CTG    3885
Ser Ile Leu Asp Asn Lys Val Glu Lys Val Val Val Ser Asn Arg Leu
            565             570                 575

GTG GAT TCG CCC TGC TGC ATT GTC ACT TCG CAG TTC GGC TGG TCC GCT    3933
Val Asp Ser Pro Cys Cys Ile Val Thr Ser Gln Phe Gly Trp Ser Ala
            580             585                 590

AAC ATG GAG CGC ATC ATG AAG GCC CAG GCT CTG CGT GAT ACC GCC ACA    3981
Asn Met Glu Arg Ile Met Lys Ala Gln Ala Leu Arg Asp Thr Ala Thr
            595             600                 605

ATG GGC TAC ATG GCC GGC AAG AAG CAG CTG GAG ATC AAC CCC GAT CAC    4029
Met Gly Tyr Met Ala Gly Lys Lys Gln Leu Glu Ile Asn Pro Asp His
610             615                 620                 625

CCA ATT GTG GAG ACT CTC CGC CAG AAG GCC GAT GCC GAC AAG AAC GAT    4077
Pro Ile Val Glu Thr Leu Arg Gln Lys Ala Asp Ala Asp Lys Asn Asp
            630                 635                 640

AAG GCC GTC AAG GAT CTG GTC ATC CTG CTG TTC GAG ACC TCT CTG CTG    4125
Lys Ala Val Lys Asp Leu Val Ile Leu Leu Phe Glu Thr Ser Leu Leu
            645                 650                 655

TCC TCT GGA TTC TCG CTG GAC AGC CCC CAG GTG CAC GCC AGC CGC ATC    4173
Ser Ser Gly Phe Ser Leu Asp Ser Pro Gln Val His Ala Ser Arg Ile
            660                 665                 670

TAC CGC ATG ATC AAG CTG GGC TTG GGA ATC GAC GAG GAC GAG CCT ATG    4221
Tyr Arg Met Ile Lys Leu Gly Leu Gly Ile Asp Glu Asp Glu Pro Met
            675                 680                 685

ACT ACC GAC GAT GCC CAG AGC GCC GGA GAT GCC CCC TCG CTG GTT GAG    4269
Thr Thr Asp Asp Ala Gln Ser Ala Gly Asp Ala Pro Ser Leu Val Glu
690                 695                 700                 705

GAC ACC GAG GAC GCT TCC CAC ATG GAG GAG GTC GAT TAAGCGACCA GTCGAA    4321
Asp Thr Glu Asp Ala Ser His Met Glu Glu Val Asp
            710                 715

FIG.1E

```
ACAAACAACC AAAATTCATT CTATCACTCG CATTCACATA CACAATTTAC TTGCGTTTCG  4381
AACTTTTATA CTGAGTTTAC TACGGCCGAG TTAAATTTTG TATTCATTAA CATTTTGCCG  4441
CGTTATAAGC GACAGACATA CGCTTAACTC ATAAAAAAGC AGGAATAACT CGTTAAATGG  4501
TTAGGTTCTC ACAGAACATT CAAGAGCAGT TGTCGTTTTA AGAACTTATA ATTTAGAATC  4561
CAAGTAATTT ATGTAAAAAA CTAAAGACTA CATACGCGCC CTAGTTGGTA GAGCTATATA  4621
AAGAATCGAG TATATATATA ATTAAGGTTT GATGACCCGA TCGATGATAA ACATAAAACC  4681
AAATAAACAA CAAGCAAATG TGTTTTAAAA ATCTAACTTC TGAGCGAGTA TTTATTGGGG  4741
GGAATAAACA ATCTATGAAT CGGATTCTTT GCGCAGCAGC TGCTCAATGG CCTCCACCGT  4801
GGACACTCCG TTGGTTATCA TTATTATCTT GTTTCGCGAT CGAGATCCCT TGTCCAAAGA  4861
AACGTCGCTC TTTCGAAGAC CTAGAACTTT CGACAGAAAC TTGACCAGTT CGGCGTTAGC  4921
TTCTCCCTCG CTGGGCGGAG CGGCGATTTG GACGCCCACT CCTTCAAAGC CAATTCCTGT  4981
GATTCCGTTC TGCTTAGCCC CCGGCTTGGC AAGGATTTGT ATG                    5024
```

FIG. 1F

```
CAGTTGCTTC AGCGTCCCGG TGTGGCTGTG CCGTTGGTCC TGTGCGGTCA CTTAGCCAAG    60
ATG CCT GAG GAA ACC CAG ACC CAA GAC CAA CCG ATG GAG GAG GAG GAG    108
Met Pro Glu Glu Thr Gln Thr Gln Asp Gln Pro Met Glu Glu Glu Glu
 1           5                  10                  15

GTT GAG ACG TTC GCC TTT CAG GCA GAA ATT GCC CAG TTG ATG TCA TTG    156
Val Glu Thr Phe Ala Phe Gln Ala Glu Ile Ala Gln Leu Met Ser Leu
             20                  25                  30

ATC ATC AAT ACT TTC TAC TCG AAC AAA GAG ATC TTT CTG AGA GAG CTC    204
Ile Ile Asn Thr Phe Tyr Ser Asn Lys Glu Ile Phe Leu Arg Glu Leu
             35                  40                  45

ATT TCA AAT TCA TCA GAT GCA TTG GAC AAA ATC CGG TAT GAA ACT TTG    252
Ile Ser Asn Ser Ser Asp Ala Leu Asp Lys Ile Arg Tyr Glu Thr Leu
         50                  55                  60

ACA GAT CCC AGT AAA TTA GAC TCT GGG AAA GAG CTG CAT ATT AAC CTT    300
Thr Asp Pro Ser Lys Leu Asp Ser Gly Lys Glu Leu His Ile Asn Leu
65                  70                  75                  80

ATA CCG AAC AAA CAA GAT CGA ACT CTC ACT ATT GTG GAT ACT GGA ATT    348
Ile Pro Asn Lys Gln Asp Arg Thr Leu Thr Ile Val Asp Thr Gly Ile
                 85                  90                  95

GGA ATG ACC AAG GCT GAC TTG ATC AAT AAC CTT GGT ACT ATC GCC AAG    396
Gly Met Thr Lys Ala Asp Leu Ile Asn Asn Leu Gly Thr Ile Ala Lys
                100                 105                 110

TCT GGG ACC AAA GCG TTC ATG GAA GCT TTG CAG GCT GGT GCA GAT ATC    444
Ser Gly Thr Lys Ala Phe Met Glu Ala Leu Gln Ala Gly Ala Asp Ile
             115                 120                 125

TCT ATG ATT GGC CAG TTC GGT GTT GGT TTT TAT TCT GCT TAT TTG GTT    492
Ser Met Ile Gly Gln Phe Gly Val Gly Phe Tyr Ser Ala Tyr Leu Val
         130                 135                 140

GCT GAG AAA GTA ACT GTG ATC ACC AAA CAT AAC GAT GAT GAG CAG TAC    540
Ala Glu Lys Val Thr Val Ile Thr Lys His Asn Asp Asp Glu Gln Tyr
145                 150                 155                 160
```

FIG.2A

```
GCT TGG GAG TCC TCA GCA GGG GGA TCA TTC ACA GTG AGG ACA GAC ACA       588
Ala Trp Glu Ser Ser Ala Gly Gly Ser Phe Thr Val Arg Thr Asp Thr
                165                 170                 175

GGT GAA CCT ATG GGT CGT GGA ACA AAA GTT ATC CTA CAC CTG AAA GAA       636
Gly Glu Pro Met Gly Arg Gly Thr Lys Val Ile Leu His Leu Lys Glu
            180                 185                 190

GAC CAA ACT GAG TAC TTG GAG GAA CGA AGA ATA AAG GAG ATT GTG AAG       684
Asp Gln Thr Glu Tyr Leu Glu Glu Arg Arg Ile Lys Glu Ile Val Lys
            195                 200                 205

AAA CAT TCT CAG TTT ATT GGA TAT CCC ATT ACT CTT TTT GTG GAG AAG       732
Lys His Ser Gln Phe Ile Gly Tyr Pro Ile Thr Leu Phe Val Glu Lys
        210                 215                 220

GAA CGT GAT AAA GAA GTA AGC GAT GAT GAG GCT GAA GAA AAG GAA GAC       780
Glu Arg Asp Lys Glu Val Ser Asp Asp Glu Ala Glu Glu Lys Glu Asp
225                 230                 235                 240

AAA GAA GAA GAA AAA GAA AAA GAA GAG AAA GAG TCG GAA GAC AAA CCT       828
Lys Glu Glu Glu Lys Glu Lys Glu Glu Lys Glu Ser Glu Asp Lys Pro
                245                 250                 255

GAA ATT GAA GAT GTT GGT TCT GAT GAG GAA GAA GAA AAG AAG GAT GGT       876
Glu Ile Glu Asp Val Gly Ser Asp Glu Glu Glu Glu Lys Lys Asp Gly
            260                 265                 270

GAC AAG AAG AAG AAG AAG AAG ATT AAG GAA AAG TAC ATC GAT CAA GAA       924
Asp Lys Lys Lys Lys Lys Lys Ile Lys Glu Lys Tyr Ile Asp Gln Glu
        275                 280                 285

GAG CTC AAC AAA ACA AAG CCC ATC TGG ACC AGA AAT CCC GAC GAT ATT       972
Glu Leu Asn Lys Thr Lys Pro Ile Trp Thr Arg Asn Pro Asp Asp Ile
    290                 295                 300

ACT AAT GAG GAG TAC GGA GAA TTC TAT AAG AGC TTG ACC AAT GAC TGG      1020
Thr Asn Glu Glu Tyr Gly Glu Phe Tyr Lys Ser Leu Thr Asn Asp Trp
305                 310                 315                 320

GAA GAT CAC TTG GCA GTG AAG CAT TTT TCA GTT GAA GGA CAG TTG GAA      1068
Glu Asp His Leu Ala Val Lys His Phe Ser Val Glu Gly Gln Leu Glu
                325                 330                 335
```

FIG.2B

```
TTC AGA GCC CTT CTA TTT GTC CCA CGA CGT GCT CCT TTT GAT CTG TTT    1116
Phe Arg Ala Leu Leu Phe Val Pro Arg Arg Ala Pro Phe Asp Leu Phe
            340                 345                 350

GAA AAC AGA AAG AAA AAG AAC AAT ATC AAA TTG TAT GTA CGC AGA GTT    1164
Glu Asn Arg Lys Lys Lys Asn Asn Ile Lys Leu Tyr Val Arg Arg Val
            355                 360                 365

TTC ATC ATG GAT AAC TGT GAG GAG CTA ATC CCT GAA TAT CTG AAC TTC    1212
Phe Ile Met Asp Asn Cys Glu Glu Leu Ile Pro Glu Tyr Leu Asn Phe
            370                 375                 380

ATT AGA GGG GTG GTA GAC TCG GAG GAT CTC CCT CTA AAC ATA TCC CGT    1260
Ile Arg Gly Val Val Asp Ser Glu Asp Leu Pro Leu Asn Ile Ser Arg
385                 390                 395                 400

GAG ATG TTG CAA CAA AGC AAA ATT TTG AAA GTT ATC AGG AAG AAT TTG    1308
Glu Met Leu Gln Gln Ser Lys Ile Leu Lys Val Ile Arg Lys Asn Leu
                405                 410                 415

GTC AAA AAA TGC TTA GAA CTC TTT ACT GAA CTG GCG GAA GAT AAA GAG    1356
Val Lys Lys Cys Leu Glu Leu Phe Thr Glu Leu Ala Glu Asp Lys Glu
            420                 425                 430

AAC TAC AAG AAA TTC TAT GAG CAG TTC TCT AAA AAC ATA AAG CTT GGA    1404
Asn Tyr Lys Lys Phe Tyr Glu Gln Phe Ser Lys Asn Ile Lys Leu Gly
            435                 440                 445

ATA CAC GAA GAC TCT CAA AAT CGG AAG AAG CTT TCA GAG CTG TTA AGG    1452
Ile His Glu Asp Ser Gln Asn Arg Lys Lys Leu Ser Glu Leu Leu Arg
        450                 455                 460

TAC TAC ACA TCT GCC TCT GGT GAT GAG ATG GTT TCT CTC AAG GAC TAC    1500
Tyr Tyr Thr Ser Ala Ser Gly Asp Glu Met Val Ser Leu Lys Asp Tyr
465                 470                 475                 480

TGC ACC AGA ATG AAG GAG AAC CAG AAA CAT ATC TAT TAT ATC ACA GGT    1548
Cys Thr Arg Met Lys Glu Asn Gln Lys His Ile Tyr Tyr Ile Thr Gly
                485                 490                 495

GAG ACC AAG GAC CAG GTA GCT AAC TCA GCC TTT GTG GAA CGT CTT CGG    1596
Glu Thr Lys Asp Gln Val Ala Asn Ser Ala Phe Val Glu Arg Leu Arg
            500                 505                 510
```

FIG.2C

```
AAA CAT GGC TTA GAA GTG ATC TAT ATG ATT GAG CCC ATT GAT GAG TAC    1644
Lys His Gly Leu Glu Val Ile Tyr Met Ile Glu Pro Ile Asp Glu Tyr
        515             520             525

TGT GTC CAA CAG CTG AAG GAA TTT GAG GGG AAG ACT TTA GTG TCA GTC    1692
Cys Val Gln Gln Leu Lys Glu Phe Glu Gly Lys Thr Leu Val Ser Val
        530             535             540

ACC AAA GAA GGC CTG GAA CTT CCA GAG GAT GAA GAA GAG AAA AAG AAG    1740
Thr Lys Glu Gly Leu Glu Leu Pro Glu Asp Glu Glu Glu Lys Lys Lys
545             550             555             560

CAG GAA GAG AAA AAA ACA AAG TTT GAG AAC CTC TGC AAA ATC ATG AAA    1788
Gln Glu Glu Lys Lys Thr Lys Phe Glu Asn Leu Cys Lys Ile Met Lys
                565             570             575

GAC ATA TTG GAG AAA AAA GTT GAA AAG GTG GTT GTG TCA AAC CGA TTG    1836
Asp Ile Leu Glu Lys Lys Val Glu Lys Val Val Val Ser Asn Arg Leu
        580             585             590

GTG ACA TCT CCA TGC TGT ATT GTC ACA AGC ACA TAT GGC TGG ACA GCA    1884
Val Thr Ser Pro Cys Cys Ile Val Thr Ser Thr Tyr Gly Trp Thr Ala
        595             600             605

AAC ATG GAG AGA ATC ATG AAA GCT CAA GCC CTA AGA GAC AAC TCA ACA    1932
Asn Met Glu Arg Ile Met Lys Ala Gln Ala Leu Arg Asp Asn Ser Thr
        610             615             620

ATG GGT TAC ATG GCA GCA AAG AAA CAC CTG GAG ATA AAC CCT GAC CAT    1980
Met Gly Tyr Met Ala Ala Lys Lys His Leu Glu Ile Asn Pro Asp His
625             630             635             640

TCC ATT ATT GAG ACC TTA AGG CAA AAG GCA GAG GCT GAT AAG AAC GAC    2028
Ser Ile Ile Glu Thr Leu Arg Gln Lys Ala Glu Ala Asp Lys Asn Asp
            645             650             655

AAG TC7 GTG AAG GAT CTG GTC ATC TTG CTT TAT GAA ACT GCG CTC CTG    2076
Lys Ser Val Lys Asp Leu Val Ile Leu Leu Tyr Glu Thr Ala Leu Leu
        660             665             670

TCT TCT GGC TTC AGT CTG GAA GAT CCC CAG ACA CAT GCT AAC AGG ATC    2124
Ser Ser Gly Phe Ser Leu Glu Asp Pro Gln Thr His Ala Asn Arg Ile
        675             680             685
```

FIG.2D

```
TAC AGG ATG ATC AAA CTT GGT CTG GGT ATT GAT GAA GAT GAC CCT ACT    2172
Tyr Arg Met Ile Lys Leu Gly Leu Gly Ile Asp Glu Asp Asp Pro Thr
    690                 695                 700

GCT GAT GAT ACC AGT GCT GCT GTA ACT GAA GAA ATG CCA CCC CTT GAA    2220
Ala Asp Asp Thr Ser Ala Ala Val Thr Glu Glu Met Pro Pro Leu Glu
705                 710                 715                 720

GGA GAT GAC GAC ACA TCA CGC ATG GAA GAA GTA GAC TAATCTCTGG CTGAGG  2272
Gly Asp Asp Asp Thr Ser Arg Met Glu Glu Val Asp
            725                 730

GATGACTTAC CTGTTCAGTA CTCTACAATT CCTCTGATAA TATATTTTCA AGGATGTTTT  2332
TCTTTATTTT TGTTAATATT AAAAAGTCTG TATGGCATGA CAACTACTTT AAGGGGAAGA  2392
TAAGATTTCT GTCTACTAAG TGATGCTGTG ATACCTTAGG CACTAAAGCA GAGCTAGTAA  2452
TGCTTTTTGA GTTTCATGTT GGTTCTTTCA CAGATGGGGT AACGTGCACT GTAAGACGTA  2512
TGTAACATGA TGTTAACTTT GTGTGGTCTA AAGTGTTTAG CTGTCAAGCC GGATGCCTAA  2572
GTAGACCAAA TCTTGTTATT GAAGTGTTCT GAGCTGTATC TTGATGTTTA GAAAAGTATT  2632
CGTTACATCT TGTAGGATCT ACTTTTTGAA CTTTTCATTC CCTGTAGTTG ACAATTCTGC  2692
ATGTACTAGT CCTCTAGAAA TAGGTTAAAC TGAAGCAACT TGATGGAAGG ATCTCTCCAC  2752
AGGGCTTGTT TTCCAAAGAA AAGTATTGTT TGGAGGAGCA AAGTTAAAAG CCTACCTAAG  2812
CATATCGTAA AGCTGTTCAA ATACTCGAGC CCAGTCTTGT GGATGGAAAT GTAGTGCTCG  2872
AGTCACATTC GCTTAAAGT  TGTAACAAAT ACAGATGAGT                        2912
```

FIG.2E

```
CTCCGGCGCA GTGTTGGGAC TGTCTGGGTA TCGGAAAGCA AGCCTACGTT GCTCACTATT     60
ACGTATAATC CTTTTCTTTT CAAG ATG CCT GAG GAA GTG CAC CAT GGA GAG       111
               Met Pro Glu Glu Val His His Gly Glu
                 1               5

GAG GAG GTG GAG ACT TTT GCC TTT CAG GCA GAA ATT GCC CAA CTC ATG     159
Glu Glu Val Glu Thr Phe Ala Phe Gln Ala Glu Ile Ala Gln Leu Met
 10              15                  20                  25

TCC CTC ATC ATC AAT ACC TTC TAT TCC AAC AAG GAG ATT TTC CTT CGG     207
Ser Leu Ile Ile Asn Thr Phe Tyr Ser Asn Lys Glu Ile Phe Leu Arg
                 30                  35                  40

GAG TTG ATC TCT AAT GCT TCT GAT GCC TTG GAC AAG ATT CGC TAT GAG     255
Glu Leu Ile Ser Asn Ala Ser Asp Ala Leu Asp Lys Ile Arg Tyr Glu
                 45                  50                  55

AGC CTG ACA GAC CCT TCG AAG TTG GAC AGT GGT AAA GAG CTG AAA ATT     303
Ser Leu Thr Asp Pro Ser Lys Leu Asp Ser Gly Lys Glu Leu Lys Ile
                 60                  65                  70

GAC ATC ATC CCC AAC CCT CAG GAA CGT ACC CTG ACT TTG GTA GAC ACA     351
Asp Ile Ile Pro Asn Pro Gln Glu Arg Thr Leu Thr Leu Val Asp Thr
             75                  80                  85

GGC ATT GGC ATG ACC AAA GCT GAT CTC ATA AAT AAT TTG GGA ACC ATT     399
Gly Ile Gly Met Thr Lys Ala Asp Leu Ile Asn Asn Leu Gly Thr Ile
 90                  95                 100                 105

GCC AAG TCT GGT ACT AAA GCA TTC ATG GAG GCT CTT CAG GCT GGT GCA     447
Ala Lys Ser Gly Thr Lys Ala Phe Met Glu Ala Leu Gln Ala Gly Ala
                110                 115                 120

GAC ATC TCC ATG ATT GGG CAG TTT GGT GTT GGC TTT TAT TCT GCC TAC     495
Asp Ile Ser Met Ile Gly Gln Phe Gly Val Gly Phe Tyr Ser Ala Tyr
                125                 130                 135

TTG GTG GCA GAG AAA GTG GTT GTG ATC AGA AAG CAC AAC GAT GAT GAA     543
Leu Val Ala Glu Lys Val Val Val Ile Arg Lys His Asn Asp Asp Glu
                140                 145                 150
```

FIG. 3A

```
CAG TAT GCT TGG GAG TCT TCT GCT GGA GGT TCC TTC ACT GTG CGT GCT    591
Gln Tyr Ala Trp Glu Ser Ser Ala Gly Gly Ser Phe Thr Val Arg Ala
    155                 160                 165

GAC CAT GGT GAG CCC ATT GGC ATG GGT ACC AAA GTG ATC CTC CAT CTT    639
Asp His Gly Glu Pro Ile Gly Met Gly Thr Lys Val Ile Leu His Leu
170                 175                 180                 185

AAA GAA GAT CAG ACA GAG TAC CTA GAA GAG AGG CGG GTC AAA GAA GTA    687
Lys Glu Asp Gln Thr Glu Tyr Leu Glu Glu Arg Arg Val Lys Glu Val
                190                 195                 200

GTG AAG AAG CAT TCT CAG TTC ATA GGC TAT CCC ATC ACC CTT TAT TTG    735
Val Lys Lys His Ser Gln Phe Ile Gly Tyr Pro Ile Thr Leu Tyr Leu
            205                 210                 215

GAG AAG GAA CGA GAG AAG GAA ATT AGT GAT GAT GAG GCA GAG GAA GAG    783
Glu Lys Glu Arg Glu Lys Glu Ile Ser Asp Asp Glu Ala Glu Glu Glu
                220                 225                 230

AAA GGT GAG AAA GAA GAG GAA GAT AAA GAT GAT GAA GAA AAG CCC AAG    831
Lys Gly Glu Lys Glu Glu Glu Asp Lys Asp Asp Glu Glu Lys Pro Lys
        235                 240                 245

ATC GAA GAT GTG GGT TCA GAT GAG GAG GAT GAC AGC GGT AAG GAT AAG    879
Ile Glu Asp Val Gly Ser Asp Glu Glu Asp Asp Ser Gly Lys Asp Lys
250                 255                 260                 265

AAG AAG AAA ACT AAG AAG ATC AAA GAG AAA TAC ATT GAT CAG GAA GAA    927
Lys Lys Lys Thr Lys Lys Ile Lys Glu Lys Tyr Ile Asp Gln Glu Glu
                270                 275                 280

CTA AAC AAG ACC AAG CCT ATT TGG ACC AGA AAC CCT GAT GAC ATC ACC    975
Leu Asn Lys Thr Lys Pro Ile Trp Thr Arg Asn Pro Asp Asp Ile Thr
            285                 290                 295

CAA GAG GAG TAT GGA GAA TTC TAC AAG AGC CTC ACT AAT GAC TGG GAA   1023
Gln Glu Glu Tyr Gly Glu Phe Tyr Lys Ser Leu Thr Asn Asp Trp Glu
                300                 305                 310

GAC CAC TTG GCA GTC AAG CAC TTT TCT GTA GAA GGT CAG TTG GAA TTC   1071
Asp His Leu Ala Val Lys His Phe Ser Val Glu Gly Gln Leu Glu Phe
        315                 320                 325
```

FIG.3B

```
AGG GCA TTG CTA TTT ATT CCT CGT CGG GCT CCC TTT GAC CTT TTT GAG    1119
Arg Ala Leu Leu Phe Ile Pro Arg Arg Ala Pro Phe Asp Leu Phe Glu
330             335             340             345

AAC AAG AAG AAA AAG AAC AAC ATC AAA CTC TAT GTC CGC CGT GTG TTC    1167
Asn Lys Lys Lys Lys Asn Asn Ile Lys Leu Tyr Val Arg Arg Val Phe
                350             355             360

ATC ATG GAC AGC TGT GAT GAG TTG ATA CCA GAG TAT CTC AAT TTT ATC    1215
Ile Met Asp Ser Cys Asp Glu Leu Ile Pro Glu Tyr Leu Asn Phe Ile
            365             370             375

CGT GGT GTG GTT GAC TCT GAG GAT CTG CCC CTG AAC ATC TCC CGA GAA    1263
Arg Gly Val Val Asp Ser Glu Asp Leu Pro Leu Asn Ile Ser Arg Glu
        380             385             390

ATG CTC CAG CAG AGC AAA ATC TTG AAA GTC ATT CGC AAA AAC ATT GTT    1311
Met Leu Gln Gln Ser Lys Ile Leu Lys Val Ile Arg Lys Asn Ile Val
    395             400             405

AAG AAG TGC CTT GAG CTC TTC TCT GAG CTG GCA GAA GAC AAG GAG AAT    1359
Lys Lys Cys Leu Glu Leu Phe Ser Glu Leu Ala Glu Asp Lys Glu Asn
410             415             420             425

TAC AAG AAA TTC TAT GAG GCA TTC TCT AAA AAT CTC AAG CTT GGA ATC    1407
Tyr Lys Lys Phe Tyr Glu Ala Phe Ser Lys Asn Leu Lys Leu Gly Ile
                430             435             440

CAC GAA GAC TCC ACT AAC CGC CGC CGC CTG TCT GAG CTG CTG CGC TAT    1455
His Glu Asp Ser Thr Asn Arg Arg Arg Leu Ser Glu Leu Leu Arg Tyr
            445             450             455

CAT ACC TCC CAG TCT GGA GAT GAG ATG ACA TCT CTG TCA GAG TAT GTT    1503
His Thr Ser Gln Ser Gly Asp Glu Met Thr Ser Leu Ser Glu Tyr Val
        460             465             470

TCT CGC ATG AAG GAG ACA CAG AAG TCC ATC TAT TAC ATC ACT GGT GAG    1551
Ser Arg Met Lys Glu Thr Gln Lys Ser Ile Tyr Tyr Ile Thr Gly Glu
    475             480             485

AGC AAA GAG CAG GTG GCC AAC TCA GCT TTT GTG GAG CGA GTG CGG AAA    1599
Ser Lys Glu Gln Val Ala Asn Ser Ala Phe Val Glu Arg Val Arg Lys
490             495             500             505
```

FIG.3C

```
CGG GGC TTC GAG GTG GTA TAT ATG ACC GAG CCC ATT GAC GAG TAC TGT    1647
Arg Gly Phe Glu Val Val Tyr Met Thr Glu Pro Ile Asp Glu Tyr Cys
            510             515             520

GTG CAG CAG CTC AAG GAA TTT GAT GGG AAG AGC CTG GTC TCA GTT ACC    1695
Val Gln Gln Leu Lys Glu Phe Asp Gly Lys Ser Leu Val Ser Val Thr
        525             530             535

AAG GAG GGT CTG GAG CTG CCT GAG GAT GAG GAG GAG AAG AAG AAG ATG    1743
Lys Glu Gly Leu Glu Leu Pro Glu Asp Glu Glu Glu Lys Lys Lys Met
        540             545             550

GAA GAG AGC AAG GCA AAG TTT GAG AAC CTC TGC AAG CTC ATG AAA GAA    1791
Glu Glu Ser Lys Ala Lys Phe Glu Asn Leu Cys Lys Leu Met Lys Glu
        555             560             565

ATC TTA GAT AAG AAG GTT GAG AAG GTG ACA ATC TCC AAT AGA CTT GTG    1839
Ile Leu Asp Lys Lys Val Glu Lys Val Thr Ile Ser Asn Arg Leu Val
570             575             580             585

TCT TCA CCT TGC TGC ATT GTG ACC AGC ACC TAC GGC TGG ACA GCC AAT    1887
Ser Ser Pro Cys Cys Ile Val Thr Ser Thr Tyr Gly Trp Thr Ala Asn
            590             595             600

ATG GAG CGG ATC ATG AAA GCC CAG GCA CTT CGG GAC AAC TCC ACC ATG    1935
Met Glu Arg Ile Met Lys Ala Gln Ala Leu Arg Asp Asn Ser Thr Met
            605             610             615

GGC TAT ATG ATG GCC AAA AAG CAC CTG GAG ATC AAC CCT GAC CAC CCC    1983
Gly Tyr Met Met Ala Lys Lys His Leu Glu Ile Asn Pro Asp His Pro
            620             625             630

ATT GTG GAG ACG CTG CGG CAG AAG GCT GAG GCC GAC AAG AAT GAT AAG    2031
Ile Val Glu Thr Leu Arg Gln Lys Ala Glu Ala Asp Lys Asn Asp Lys
            635             640             645

GCA GTT AAG GAC CTG GTG GTG CTG CTG TTT GAA ACC GCC CTG CTA TCT    2079
Ala Val Lys Asp Leu Val Val Leu Leu Phe Glu Thr Ala Leu Leu Ser
650             655             660             665

TCT GGC TTT TCC CTT GAG GAT CCC CAG ACC CAC TCC AAC CGC ATC TAT    2127
Ser Gly Phe Ser Leu Glu Asp Pro Gln Thr His Ser Asn Arg Ile Tyr
            670             675             680
```

FIG.3D

```
CGC ATG ATC AAG CTA GGT CTA GGT ATT GAT GAA GAT GAA GTG GCA GCA     2175
Arg Met Ile Lys Leu Gly Leu Gly Ile Asp Glu Asp Glu Val Ala Ala
            685             690             695

GAG GAA CCC AAT GCT GCA GTT CCT GAT GAG ATC CCC CCT CTC GAG GGC     2223
Glu Glu Pro Asn Ala Ala Val Pro Asp Glu Ile Pro Pro Leu Glu Gly
    700             705             710

GAT GAG GAT GCG TCT CGC ATG GAA GAA GTC GAT TAGGTTAGGA GTTCATAGTT   2276
Asp Glu Asp Ala Ser Arg Met Glu Glu Val Asp
    715             720

GGAAAACTTG TGCCCTTGTA TAGTGTCCCC ATGGGCTCCC ACTGCAGCCT CGAGTGCCCC   2336
TGTCCCACCT GGCTCCCCCT GCTGGTGTCT AGTGTTTTTT TCCCTCTCCT GTCCTTGTGT   2396
TGAAGGCAGT AAACTAAGGG TGTCAAGCCC CATTCCCTCT CTACTCTTGA CAGCAGGATT   2456
GGATGTTGTG TATTGTGGTT TATTTTATTT TCTTCATTTT GTTCTGAAAT TAAAGTATGC   2516
AAAATAAAGA ATATGCCGTT TTTATAC                                       2543
```

FIG. 3E

METHOD BASED ON LOCALIZATION OF HSP90 TO THE CENTROSOME

1. FIELD OF THE INVENTION

The present invention is directed to methods for screening for fragments and derivatives of Hsp90 that are altered in their subcellular localization, and thus, altered in their activity as compared to wild type Hsp90. The present invention is also directed to screening for modulators of Hsp90 activity as determined by assaying for altered subcellular localization of Hsp90. The present invention is further directed to diagnostic, prognostic and screening uses of Hsp90/centrosome co-purification.

2. BACKGROUND OF THE INVENTION

The Hsp90 family of proteins is a group of highly conserved stress proteins that are expressed in all eukaryotic cells, and are essential in yeast and Drosophila. For a general review of heat shock proteins, see Parsell and Lindquist, 1993, Ann. Rev. Genet. 27:437–496. Hsp90 is one of the most abundant proteins in the eukaryotic cell, constituting up to about 1–2% of the cellular protein under normal physiologic conditions, and its expression is increased several-fold in response to stress. Up to now, members of the Hsp90 family were found in the cytosol, the endoplasmic reticulum, and chloroplasts; however, evidence for the actual subcellular localization in the cell or possible association with cellular organelles has so far been cryptic and at best contradictory. Scheibel and Buchner, 1997, The Hsp90 Family—An Overview, In: *Guidebook to Molecular Chaperones and Protein Catalysts*, Oxford University Press, pp. 147–151. Although family members of Hsp90 have interchangeable functions, the respective genes are differentially regulated in eukaryotes. Borkovich et al., 1989, Mol. Cell Biol. 9:3919–3930. In most eukaryotic cells, one of the two Hsp90 family members is expressed constitutively at a high level at physiological temperature and is induced only 2–3 times by heat shock. A second family member is expressed at a low basal level at normal temperatures, but its expression is enhanced strongly under restrictive growth conditions, like heat treatment. See, Borkovich et al., 1989, Mol. Cell Biol. 9:3919–3930; Krone and Sass, 1994, Biochem. Biophys. Res. Commun. 204:746–752.

The two genes that encode Hsp90 in humans, Hsp90α and Hsp90β, are 86% homologous. Further, there is extensive homology with lower species. The 63 kDa Hsp90 homolog in *Escherichia coli* is 42% identical in amino acid sequence to human Hsp90. The 83 kDa Hsp90 protein homolog of Drosophila (Hsp83) is 78% identical/similar to human Hsp90. See, e.g., Alique et al., 1994, EMBO J. 13:6099–6106; Rebbe et al., 1987, Gene 53:235–245; Blackman et al., 1986, J. Mol. Biol. 188:499–515.

The Hsp90 family has been implicated as an important component of intracellular signaling pathways as well as in assisting protein folding. Dimeric Hsp90 proteins bind molecules such as steroid hormone receptors and the receptor kinases v-src, Raf, and casein kinase II (Catelli et al., 1985, EMBO J. 4:3131–3135; Miyata and Yahara, 1992, J. Biol. Chem. 267:7042–7047; Stancato et al., 1993, J. Biol. Chem. 268:21711–21716; Xu and Lindquist, 1993, Proc. Natl. Acad. Sci, USA 90:7074–7078; Wartmann and Davis, 1994, J. Biol. Chem. 269:6695–6701; van der Straten et al., 1997, EMBO J. 16:1961–1969). In the case of steroid receptors, this interaction is required for efficient ligand binding and transcriptional regulation (Bohen and Yamamoto, 1994, Modulation of Steroid Receptor Signal Transduction by Heat Shock Proteins, In: *The Biology of Heat Shock Proteins and Molecular Chaperones*, Cold Spring Harbor Laboratory Press, pp. 313–334).

Although the molecular structure of Hsp90 is known in detail and a long list of interacting partners is known, very little is known about the subcellular localization of Hsp90 except that Hsp90 is observed in the cytoplasm and nucleus.

Citation or identification of any reference in Section 2 or in any other section of this application shall not be construed as an admission that such reference is available as prior art to the present invention.

3. SUMMARY OF THE INVENTION

The present inventors have discovered that at least a significant portion of the Hsp90 molecules in a cell are localized to, and are a core component of (tightly associated with) the centrosome. Further, the localization of Hsp90 to the centrosome, and thus, its function and role in mitosis and fidelity of chromosome segregation, is conserved over evolution. Hsp90 is known to play important roles in the control of cell signaling and the cell cycle, as well as in transcription, therefore the detection of fragments and derivatives of Hsp90 that have altered localization identifies those Hsp90 molecules that have different activities, and allows for the screening of molecules that alter Hsp90 activity by altering its location.

The present invention is directed to methods of identifying a molecule that alters the centrosomal location of Hsp90 in a cell comprising the following steps in the order stated: (a) contacting the cell with one or more candidate molecules; and (b) detecting localization of Hsp90 molecules in the cell, wherein an increase or decrease in the amount of Hsp90 localized to the centrosome relative to said amount in a cell not so contacted with the one or more candidate molecules indicates that the candidate molecules alter the centrosomal localization of Hsp90. In another embodiment, the present invention is directed to methods of identifying a molecule that alters the centrosomal location of Hsp90 in a cell comprising the following steps in the order stated: (a) recombinantly expressing within the cell one or more candidate molecules; and (b) detecting localization of Hsp90 molecules in the cell, wherein an increase or decrease in the amount of Hsp90 localized to the centrosome relative to said amount in a cell in which the one or more candidate molecules were not so expressed indicates that the candidate molecules alter the centrosomal localization of Hsp90. In a specific aspect of either embodiment, step (b) comprises contacting the cell with an antibody to Hsp90 or a binding region of said antibody, and a fluorescently labeled binding partner of said antibody under conditions conducive to immunospecific binding. In an alternative aspect, the method of detecting comprises contacting the cell with a fluorescently labeled antibody to Hsp90 or a binding region of said antibody under conditions conducive to immunospecific binding. In yet another embodiment, the method of detecting comprises sequencing by mass spectroscopy centrosomal proteins isolated from the cell.

In another embodiment of the present invention, methods of identifying a molecule that affects Hsp90 function in a cell are provided which comprise the following steps in the order stated: (a) contacting the cell with one or more candidate molecules; and (b) detecting or measuring altered centrosomal or chromosomal structure or function, wherein an alteration of centrosomal or chromosomal structure or function relative to said structure or function in a cell not so contacted with the one or more candidate molecules indicates that the candidate molecules affects Hsp90 function. In an alternative embodiment, the method of identifying a molecule that affects Hsp90 function in a cell comprises the following steps in the order stated: (a) recombinantly expressing within the cell one or more candidate molecules; and (b) detecting or measuring altered centrosomal or chromosomal structure or function, wherein an alteration of centrosomal or chromosomal structure or function relative to said structure or function in a cell in which the one or more candidate molecules were not so expressed indicates that the candidate molecules affects Hsp90 function. In a specific aspect of either embodiment, the altered centrosomal or chromosomal structure or function is evidenced by an aberrant mitotic figure, which mitotic figure includes but is not limited to monopolar spindles, aneuploydies, chromosomal missegregation, or chromosome non-joinder.

In yet another embodiment, the present invention is directed to methods of identifying a derivative or fragment of Hsp90 that has altered biological activity relative to wild type Hsp90 comprising detecting a qualitative or quantitative change in intracellular location of said derivative or fragment relative to the intracellular location of wild type Hsp90.

In another embodiment, the method of identifying a molecule that alters the centrosomal location of Hsp90 in a cell comprises the following steps in the order stated: (a) microinjecting into the cell one or more candidate molecules; and (b) detecting localization of Hsp90 molecules in the cell, wherein an increase or decrease in the amount of Hsp90 localized to the centrosome relative to said amount in a cell not so microinjected with the one or more candidate molecules indicates that the candidate molecules alter the centrosomal localization of Hsp90.

The present invention also provides methods for identifying a derivative or fragment of Hsp90 which co-purifies or localizes to the centrosome in a cell comprising the following steps in the order stated: (a) contacting a derivative or fragment of Hsp90 with a cell; and (b) detecting whether said derivative or fragment co-purifies or localizes to the centrosome in said cell. The present invention also provides methods for identifying a derivative or fragment of Hsp90 which co-purifies or localizes to the centrosome in a cell comprising the following steps in the order stated: (a) recombinantly expressing a derivative or fragment of Hsp90 in a cell; and (b) detecting whether said derivative or fragment co-purifies or localizes to the centrosome in said cell. In a specific aspect of these embodiments, step (b) comprises contacting the cell with an antibody to Hsp90 or binding region of the antibody, and a fluorescently labeled binding partner of said antibody under conditions conducive to immunospecific binding. In another specific aspect, step (b) comprises contacting the cell with a fluorescently labeled antibody to Hsp90 or binding region of the antibody under conditions conducive to immunospecific binding. In yet another specific aspect, step (b) comprises sequencing by mass spectroscopy centrosomal peptides isolated from the cell.

In another embodiment of the present invention, methods for screening for a molecule that modulates directly or indirectly Hsp90 activity are provided which comprise the following steps in the order stated: (a) contacting a cell expressing Hsp90 with one or more candidate molecules; and (b) detecting the levels of Hsp90 localized to the centrosome in said cell relative to said levels in a cell not contacted with said candidate molecules, wherein a higher or lower level of Hsp90 localization to the centrosome in the presence of said candidate molecules indicates that the molecules modulate the activity of Hsp90, or which comprise the following steps in the order stated: (a) recombinantly expressing one or more candidate molecules within a cell expressing Hsp90; and (b) detecting the levels of Hsp90 localized to the centrosome in said cell relative to said levels in a cell in which candidate molecules were not so expressed, wherein a higher or lower level of Hsp90 localization to the centrosome in the presence of said candidate molecules indicates that the molecules modulate the activity of Hsp90. In one aspect of this embodiment, Hsp90 localization to the centrosome is detected by a method comprising contacting the cell with a molecule that binds to Hsp90 and a molecule that binds to a centrosome-specific protein other than Hsp90 under conditions conducive to binding, and detecting any binding of the molecules to the same subcellular location that occurs.

In yet another embodiment of the present invention, methods are provided for modulating the activity of Hsp90 by contacting a cell expressing Hsp90 with a molecule that modulates the localization of Hsp90 to the centrosome in a cell.

In yet another embodiment of the present invention, methods are provided for diagnosing or screening for the presence of or a predisposition for developing a disease or disorder characterized by aberrant Hsp90 subcellular localization in a subject by measuring the level of Hsp90 localization to the centrosome in a sample derived from the subject, in which a decrease or increase in the level of centrosomal localization of Hsp90 relative to the level of localization in an analogous sample not having the disease or disorder or a predisposition for developing the disease or disorder indicates the presence of the disease or disorder or the predisposition for developing the disease or disorder.

4. BRIEF DESCRIPTION OF THE FIGURE

FIGS. 1A–F. The nucleotide sequence (SEQ ID NO:1) and the encoded amino acid sequence (SEQ ID NO:2) of an illustrative Drosophila Hsp83, a member of the Hsp90 family of proteins.

FIGS. 2A–E. The nucleotide sequence (SEQ ID NO:3) and the encoded amino acid sequence (SEQ ID NO:4) of an illustrative human Hsp90α.

FIGS. 3A–E. The nucleotide sequence (SEQ ID NO:5) and the encoded amino acid sequence (SEQ ID NO:6) of an illustrative human Hsp90β.

FIG. 4. Coomassie stained 10% SDS-PAGE gel of the three stages of the centrosome purification procedure. First lane, Drosophila embryo homogenate. Second lane, centrosome-enriched fraction from the sucrose density gradient. Third lane, immunopurified centrosome preparation. BSA and IgG were added during the purification procedure. Mass spectroscopy protein sequencing revealed that the major 140 kDa band corresponds to the previously characterized centrosomal protein centrosomin ("CNN"). The position of Hsp90 is also shown.

5. DETAILED DESCRIPTION OF THE INVENTION

The present inventors have discovered that at least a significant portion of the Hsp90 molecules in a cell are localized to, and are a core component of (tightly associated with) the centrosome. Further, the localization of Hsp90 to the centrosome, and thus, its function and role in mitosis and fidelity of chromosome segregation, is conserved over evolution. Hsp90 is known to play important roles in the control of cell signaling and the cell cycle, as well as in transcription, therefore the detection of fragments and derivatives of Hsp90 that have altered localization identifies those Hsp90 molecules that have different activities, and allows for the screening of molecules that alter Hsp90 activity by altering its location.

The present invention is directed to methods of identifying a molecule that alters the centrosomal location of Hsp90 in a cell comprising the following steps in the order stated: (a) contacting the cell with one or more candidate molecules; and (b) detecting localization of Hsp90 molecules in the cell, wherein an increase or decrease in the amount of Hsp90 localized to the centrosome relative to said amount in a cell not so contacted with the one or more candidate molecules indicates that the candidate molecules alter the centrosomal localization of Hsp90. In another embodiment, the present invention is directed to methods of identifying a molecule that alters the centrosomal location of Hsp90 in a cell comprising the following steps in the order stated: (a) recombinantly expressing within the cell one or more candidate molecules; and (b) detecting localization of Hsp90 molecules in the cell, wherein an increase or decrease in the amount of Hsp90 localized to the centrosome relative to said amount in a cell in which the one or more candidate molecules were not so expressed indicates that the candidate molecules alter the centrosomal localization of Hsp90.

In another embodiment of the present invention, methods of identifying a molecule that affects Hsp90 function in a cell are provided which comprise the following steps in the order stated: (a) contacting the cell with one or more candidate molecules; and (b) detecting or measuring altered centrosomal or chromosomal structure or function, wherein an alteration of centrosomal or chromosomal structure or function relative to said structure or function in a cell not so contacted with the one or more candidate molecules indicates that the candidate molecules affects Hsp90 function. In an alternative embodiment, the method of identifying a molecule that affects Hsp90 function in a cell comprises the following steps in the order stated: (a) recombinantly expressing within the cell one or more candidate molecules; and (b) detecting or measuring altered centrosomal or chromosomal structure or function, wherein an alteration of centrosomal or chromosomal structure or function relative to said structure or function in a cell in which the one or more candidate molecules were not so expressed indicates that the candidate molecules affects Hsp90 function.

In yet another embodiment, the present invention is directed to methods of identifying a derivative or fragment of Hsp90 that has altered biological activity relative to wild type Hsp90 comprising detecting a qualitative or quantitative change in intracellular location of said derivative or fragment relative to the intracellular location of wild type Hsp90.

In another embodiment, the method of identifying a molecule that alters the centrosomal location of Hsp90 in a cell comprises the following steps in the order stated: (a) microinjecting into the cell one or more candidate molecules; and (b) detecting localization of Hsp90 molecules in the cell, wherein an increase or decrease in the amount of Hsp90 localized to the centrosome relative to said amount in a cell not so microinjected with the one or more candidate molecules indicates that the candidate molecules alter the centrosomal localization of Hsp90.

The present invention also provides methods for identifying a derivative or fragment of Hsp90 which co-purifies or localizes to the centrosome in a cell comprising the following steps in the order stated: (a) contacting a derivative or fragment of Hsp90 with a cell; and (b) detecting whether said derivative or fragment co-purifies or localizes to the centrosome in said cell. The present invention also provides methods for identifying a derivative or fragment of Hsp90 which co-purifies or localizes to the centrosome in a cell comprising the following steps in the order stated: (a) recombinantly expressing a derivative or fragment of Hsp90 in a cell; and (b) detecting whether said derivative or fragment co-purifies or localizes to the centrosome in said cell.

In another embodiment of the present invention, methods for screening for a molecule that modulates directly or indirectly Hsp90 activity are provided which comprise the following steps in the order stated: (a) contacting a cell expressing Hsp90 with one or more candidate molecules; and (b) detecting the levels of Hsp90 localized to the centrosome in said cell relative to said levels in a cell not contacted with said candidate molecules, wherein a higher or lower level of Hsp90 localization to the centrosome in the presence of said candidate molecules indicates that the molecules modulate the activity of Hsp90, or which comprise the following steps in the order stated: (a) recombinantly expressing one or more candidate molecules within a cell expressing Hsp90; and (b) detecting the levels of Hsp90 localized to the centrosome in said cell relative to said levels in a cell in which candidate molecules were not so expressed, wherein a higher or lower level of Hsp90 localization to the centrosome in the presence of said candidate molecules indicates that the molecules modulate the activity of Hsp90.

In yet another embodiment of the present invention, methods are provided for modulating the activity of Hsp90 by contacting a cell expressing Hsp90 with a molecule that modulates the localization of Hsp90 to the centrosome in a cell.

In yet another embodiment of the present invention, methods are provided for diagnosing or screening for the presence of or a predisposition for developing a disease or disorder characterized by aberrant Hsp90 subcellular localization in a subject by measuring the level of Hsp90 localization to the centrosome in a sample derived from the subject, in which a decrease or increase in the level of centrosomal localization of Hsp90 relative to the level of localization in an analogous sample not having the disease or disorder or a predisposition for developing the disease or disorder indicates the presence of the disease or disorder or the predisposition for developing the disease or disorder.

For clarity of disclosure, and not by way of limitation, a detailed description of the invention is divided into the following subsections.

5.1. DETECTION OF Hsp90 SUBCELLULAR LOCALIZATION

The Hsp90 molecules detected in accordance with the present invention include, but are not limited to, any member of the Hsp90 family of proteins, or a derivative, homolog or fragment thereof. The Hsp90 molecules can be obtained from any species, e.g., mouse, rat, pig, cow, dog, monkey, human, fly, frog, etc. The Hsp90 molecules can also be obtained from plants. In preferred embodiments, the Hsp90 molecules detected are human Hsp90 molecules or derivatives, homologs, or fragments thereof. FIGS. 1A–F, 2A–E and 3A–E set forth the nucleotide and amino acid sequences of illustrative members of the Hsp90 family of proteins. Further illustrative examples of members of the Hsp90 family of proteins are described in Krone et al., 1994, Biocehm. Biophys. Res. Commun. 204:746–752 (zebrafish Hsp90α); de Andrade et al., 1992, J. Clin. Microbiol. 30:330–335 (Leishmania); Meng et al., 1993, Biochem. Biophys. Res. Commun. 190:630–636 (chicken Hsp90β); McGuire et al., 1992, J. Steroid Biochem. Mol. Biol. 42:813–822 (rat Hsp90β); and Chen and Laszlo, 1995, direct submission to EMBL/GENBANK, Accession No. P46633 (chicken Hsp90α).

Any method known in the art for detecting the subcellular localization of Hsp90, i.e., to the centrosome, can be used in the present invention. For example, and not by way of limitation, one such method of detection is contacting a cell with an antibody specific for Hsp90 and then detecting whether the antibody localizes to the centrosome. A particular method of detecting Hsp90 subcellular localization is to contact a labeled anti-Hsp90 antibody, e.g., labeled with a fluorescent dye, and a labeled anti-centrosomin ("CNN") antibody, e.g., with a fluorescent dye different from the anti-Hsp90 antibody, to whole cells and then to detect cells having both labels co-localized in the cell by, e.g., laser scanning microscopy.

Thus, detection methods encompassed by the present invention include immunofluorescence or immunoelectron microscopy, for in situ detection of the Hsp90 molecule. In situ detection may be accomplished by contacting a cell endogenously or recombinantly expressing a Hsp90 molecule with a labeled molecule that binds to Hsp90 and detecting any binding that occurs and that is localized to the centrosome. Alternatively, an unlabeled molecule may be used, in combination with a labeled binding partner of the molecule. Using such an assay, it is possible to determine not only the presence of the Hsp90 molecule, but also its subcellular distribution, i.e., at the centrosome.

Immunoassays for Hsp90 will typically comprise incubating a sample, such as a cell in vivo or in in vitro culture, in the presence of a detectably labeled molecule specific for Hsp90, e.g., an antibody to Hsp90, and detecting the bound molecule by any of a number of techniques known in the art.

In a specific embodiment, a biological sample, e.g., freshly obtained cells, may be brought in contact with and immobilized onto a solid phase support or carrier such as nitrocellulose, glass, polystyrene, or other solid support which is capable of immobilizing cells. The support may then be washed with suitable buffers followed by treatment with the detectably labeled molecule. The solid phase support may then be washed with the buffer a second time to remove unbound molecule. The amount of bound label on solid support may then be detected by conventional means.

The binding activity of a given antibody to a Hsp90 molecule may be determined according to well known methods. Those skilled in the art will be able to determine operative and optimal assay conditions for each determination by employing routine experimentation.

One of the ways in which an antibody to Hsp90 can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller et al., 1978, J. Clin. Pathol. 31:507–520; Butler, 1981, Meth. Enzymol. 73:482–523; Maggio, E. (ed.), 1980, Enzyme Immunoassay, CRC Press, Boca Raton, Fla.,; Ishikawa et al., (eds.), 1981, Enzyme Immunoassay, Kgaku Shoin, Tokyo)). The enzyme which is bound to the antibody bound to a Hsp90 molecule will react with an appropriate substrate, preferably a chromogenic substrate, in such a manner as to produce a chemical moiety which can be detected, for example, by spectrophotometric, fluorimetric or by visual means.

It is also possible to label the antibody with a fluorescent or chemiluminescent or bioluminescent compound or with a radioactive moiety or other label known in the art.

Another method of detecting and/or measuring Hsp90 centrosomal localization is to isolate centrosomes by any method known in the art and detect whether Hsp90 is present in the centrosome complex, preferably by mass spectroscopy analysis to identify the proteins of the centrosome complex.

Isolation of centrosomes can be accomplished by, e.g., density gradient centrifugation and immuno-isolation as described in Section 6.1, infra. After centrosome isolation, detection of Hsp90 can be accomplished, e.g., by immunoprecipitating Hsp90 with an anti-Hsp90 antibody or binding to anti-Hsp90 antibody on an immunoaffinity column or immobilized on a plate or in a well, or visualizing the protein by Western blotting. In another embodiment of the invention, Hsp90 localization to the centrosome can be detected and/or measured by isolating centrosomes, separating centrosomal proteins on a SDS-PAGE gel, eluting separated protein from the gel, and subjecting the eluted protein to mass spectroscopy analysis to determine amino acid sequence. Such mass spectroscopy analysis can be carried out by any suitable method of mass spectroscopy known in the art, e.g., as described in Section 6.1, infra, as well as the method described in Neubauer et al., 1998, Nature Genetics 20:46–50; Neubauer et al., 1997, Proc. Natl. Acad. Sci. USA 94:385–390; and Wilm et al., 1996, Nature 379:466–469. By way of example but not limitation, the eluted peptides are dissolved in a 5% methanol/5% formic acid solution and desalted using a capillary column as described in Wilm and Mann, 1996, Anal. Chem. 68:1–8. The peptides are then diluted in one step in a 50% methanol/ 5% formic acid solution (0.5–2 μl) directly into the spraying needle of the nanoelectrospray ion source. A mass spectrum of the peptides is acquired. The peptides are then selected in turn in the first quadrupole. This first part of the mass spectrometer is used as a mass filter, only allowing the transmission of a peptide ion species of one m/z value at a time. Each peptide is then fragmented individually by collision-induced dissociation with argon in the collision cell. The resulting peptide fragment ions are separated in the third quadrupole and detected. For tryptic peptides this usually results in a 'nested set' of peptide fragments containing the carboxy-terminus. As the mass difference between two adjacent fragments corresponds with the residue masses of the corresponding amino acid, partial sequence of the peptide from its carboxy to amino terminus can be determined.

The cell in which the localization of Hsp90 is detected and/or measured can be in vitro (e.g., isolated in cell culture) or in vivo. The cell in which Hsp90 subcellular localization is detected can be any cell, e.g., one that endogenously or recombinantly expresses Hsp90 or a derivative or fragment or homolog thereof. (See Section 5.2.1. for recombinant expression of Hsp90 molecule.) The cell can be vertebrate, insect (e.g., Drosophila), C. elegans, mammalian, bovine, murine, rat, avian, fish, primate, human, etc. The Hsp90 which is expressed can be vertebrate, insect, C. elegans, mammalian, bovine, murine, rat, avian, fish, primate, human, etc. The cell can be a cell of primary tissue, a cell line, or of an animal containing and expressing a Hsp90 transgene. For example, the transgenic animal can be a Drosophila (e.g., melanogaster) or a *C. elegans*. In a preferred embodiment, the transgene encodes a human Hsp90. Transgenic animals can be made by standard methods well known in the art.

In specific embodiments of the invention, antibodies and fragments containing the binding domain thereof, directed against Hsp90 are used to detect Hsp90 in a specific embodiment of the above methods. Accordingly, Hsp90 proteins, fragments or analogs or derivatives thereof, in particular, human Hsp90 proteins or fragments thereof, may be used as immunogens to generate anti-Hsp90 protein antibodies. Such antibodies can be polyclonal, monoclonal, chimeric, single chain, Fab fragments, or from an Fab expression library. Methods for the production of such antibodies are well known in the art, and some of which are described in Section 5.1.1., infra.

The antibodies specific for Hsp90 can be used in methods known in the art, and those methods discussed above, relating to the localization and/or quantification of Hsp90 proteins of the invention, e.g., for imaging these proteins, measuring levels thereof in appropriate physiological samples, in diagnostic methods, etc. This hold true also for a derivative, homolog, or analog of a Hsp90 protein.

5.1.1. ANTIBODY PRODUCTION

Various procedures known in the art may be used for the production of antibodies to Hsp90, or a fragment, derivative, homolog or analog of the protein.

For production of the antibody, various host animals can be immunized by injection with a native Hsp90 or a synthetic version, or a derivative of the foregoing. Such host animals include, but are not limited to, rabbits, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacille Calmette-Guerin (BCG) and Corynebacterium parvum.

For preparation of monoclonal antibodies directed towards Hsp90 or a derivative, fragment, homolog or analog thereof, any technique that provides for the production of antibody molecules by continuous cell lines in culture may be used. Such techniques include, but are not restricted to, the hybridoma technique originally developed by Kohler and Milstein (1975, Nature 256:495–497), the trioma technique (Gustafsson et al., 1991, Hum. Antibodies Hybridomas 2:26–32), the human B-cell hybridoma technique (Kozbor et al., 1983, Immunology Today 4:72), and the EBV hybridoma technique to produce human monoclonal antibodies (Cole et al., 1985, In: Monoclonal Antibodies and Cancer Therapy, Alan R. Liss, Inc., pp. 77–96). In an additional embodiment of the invention, monoclonal antibodies can be produced in germ-free animals utilizing recent technology described in International Patent Application PCT/US90/02545.

According to the present invention, human antibodies may be used and can be obtained by using human hybridomas (Cote et al., 1983, Proc. Natl. Acad. Sci. USA 80:2026–2030) or by transforming human B cells with EBV virus in vitro (Cole et al., 1985, In: Monoclonal Antibodies and Cancer Therapy, Alan R. Liss, Inc., pp. 77–96). In fact, according to the invention, techniques developed for the production of "chimeric antibodies" (Morrison et al., 1984, Proc. Natl. Acad. Sci. USA 81:6851–6855; Neuberger et al., 1984, Nature 312:604–608; Takeda et al., 1985, Nature 314:452–454) by splicing the genes from a mouse antibody molecule specific for Hsp90 together with genes from a human antibody molecule of appropriate biological activity can be used; such antibodies are within the scope of this invention.

According to the present invention, techniques described for the production of single chain antibodies (U.S. Pat. No. 4,946,778) can be adapted to produce Hsp90-specific antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for Hsp90 proteins, derivatives, or analogs thereof. Non-human antibodies can be "humanized" by known methods (e.g., U.S. Pat. No. 5,225,539).

Antibody fragments that contain the idiotypes of Hsp90 can be generated by techniques known in the art. For example, such fragments include, but are not limited to, the F(ab')2 fragment which can be produced by pepsin digestion of the antibody molecule; the Fab' fragment that can be generated by reducing the disulfide bridges of the F(ab')2 fragment; the Fab fragment that can be generated by treating the antibody molecular with papain and a reducing agent; and Fv fragments. Synthetic antibodies, e.g., antibodies produced by chemical synthesis, are useful in the present invention.

In the production of antibodies, screening for the desired antibody can be accomplished by techniques known in the art, e.g., ELISA (enzyme-linked immunosorbent assay). To select antibodies specific to a particular domain of Hsp90, or a derivative, homolog, or analog thereof, one may assay generated hybridomas for a product that binds to the fragment of the Hsp90 protein, or a derivative, homolog, or analog thereof, that contains such a domain.

5.2. SCREENING FOR DERIVATIVES OF Hsp90 FOR ALTERED CENTROSOMAL LOCALIZATION

In one embodiment of the invention, derivatives, fragments, and analogs of Hsp90 are identified that have altered activity compared to wild type Hsp90 by detecting a change in the localization of such derivatives, fragments, or analogs relative to the location (or amount at a particular subcellular location) of wild type Hsp90. Both qualitative (a difference in localization of Hsp90) and quantitative (a difference in the amount of Hsp90 localized to a particular location) changes in Hsp90 can be detected and/or measured in accordance with the present invention. Thus, the present invention provides methods for identifying a Hsp90 fragment or derivative that has altered activity as compared to wild type Hsp90 by detecting whether said fragment or derivative co-purifies with or localizes to the centrosome comprising contacting a cell with a fragment or derivative of Hsp90 and detecting whether said fragment or derivative co-purifies with or localizes to the centrosome, wherein the lack of co-purification with or localization of the fragment or derivative to the centrosome indicates that the fragment or derivative has altered activity as compared to wild type Hsp90. The present invention also provides methods for identifying a Hsp90 fragment or derivative that has altered activity as compared to wild type Hsp90 by detecting whether said fragment or derivative co-purifies with or localizes to the centrosome comprising recombinantly expressing within a cell a fragment or derivative of Hsp90 and detecting whether said fragment or derivative co-purifies with or localizes to the centrosome, wherein the lack of co-purification with or localization of the fragment or derivative to the centrosome indicates that the fragment or derivative has altered activity as compared to wild type Hsp90. Recombinant expression of Hsp90, or a fragment or derivative thereof can be by any method known in the art, including those set forth in Section 5.2.1., infra.

The assay methods of this embodiment of the invention are preferably carried out in vitro or in cell culture, but alternatively, may be carried out in vivo in an animal, e.g., Drosophila. In one aspect of this embodiment of the invention, the derivative or fragment of Hsp90 can be synthesized or recombinantly produced and isolated before contacting the cell. In another aspect of this embodiment of the invention, nucleic acids encoding a Hsp90 fragment or derivative are introduced into a cell for expression of said fragment or derivative. In yet another aspect, contacting the cell with the derivative or fragment is carried out by microinjecting the derivative or fragment into the cell.

Detection and/or measurement of localization of the derivative or fragment the centrosome can be carried out by methods well known in the art and/or those methods disclosed in Section 5.1, supra.

Hsp90 derivatives, fragments, and analogs to be screened by the assay methods of the invention can be produced by various methods known in the art. The manipulations which result in their production can occur at the gene or protein level. For example, the cloned Hsp90 gene sequences can be modified by any of numerous strategies known in the art (Sambrook et al., 1989, Molecular Cloning, A Laboratory Manual, 2 d Ed., Cold Spring Harbor Laboratory Press, Cold Spring Harbor, N.Y.). The sequences can be cleaved at appropriate sites with restriction endonuclease(s), followed by further enzymatic modification if desired, isolated, and ligated in vitro. In the production of the gene encoding a derivative, homolog or analog of Hsp90, care should be taken to ensure that the modified gene retains the original translational reading frame, uninterrupted by translational stop signals, in the gene region where the desired activity is encoded.

Additionally, the Hsp90-encoding nucleic acid sequence can be mutated in vitro or in vivo, to create and/or destroy translation, initiation, and/or termination sequences, or to create variations in coding regions and/or form new restriction endonuclease sites or destroy pre-existing ones, to facilitate further in vitro modification. Any technique for mutagenesis known in the art can be used, including but not limited to, chemical mutagenesis and in vitro site-directed mutagenesis (Hutchinson et al., 1978, J. Biol. Chem 253:6551–6558), amplification with PCR primers containing a mutation, etc.

In a specific embodiment of the present invention, such Hsp90 fragments or derivatives, whether produced by recombinant DNA techniques, chemical synthesis methods, or by purification from native sources include, but are not limited to, those containing, as a primary amino acid sequence, all or part of the amino acid sequences substantially as depicted in FIGS. 1, 2 and 3 (SEQ ID NO:2, SEQ ID NO:4, and SEQ ID NO:6, respectively), as well as fragments and other analogs and derivatives thereof, including proteins homologous thereto.

Manipulations of Hsp90 sequences may be made at the protein level. Included within the scope of the invention is a Hsp90 fragment, derivative or analog that is differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

In specific embodiments, the Hsp90 amino acid sequences are modified to include a fluorescent label. In another specific embodiment, Hsp90 is modified to have a heterofunctional reagent; such heterofunctional reagents can be used to crosslink Hsp90 to other proteins.

In addition, analogs and derivatives of Hsp90 can be chemically synthesized. For example, a peptide corresponding to a portion of Hsp90, which comprises a desired domain or mediates a desired activity in vitro, can be synthesized by use of a peptide synthesizer. Furthermore, if desired, non-classical amino acids or chemical amino acid analogs can be introduced as a substitution or addition into the Hsp90 protein. Non-classical amino acids include but are not limited to the D-isomers of the common amino acids, α-amino isobutyric acid, 4-aminobutyric acid (4-Abu), 2-aminobutyric acid (2-Abu), 6-amino hexanoic acid (Ahx), 2-amino isobutyric acid (2-Aib), 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In particular, Hsp90 derivatives can be made by altering their sequences by substitutions, additions or deletions that provide for functionally equivalent molecules. Due to the degeneracy of nucleotide coding sequences, other DNA sequences that encode substantially the same amino acid sequence as a Hsp90 gene or cDNA can be used in the practice of the present invention. These include but are not limited to nucleotide sequences comprising all or portions of the Hsp90α and Hsp90β, genes that are altered by the substitution of different codons that encode a functionally equivalent amino acid residue within the sequence, thus producing a silent change. Likewise, the Hsp90 derivatives of the invention include, but are not limited to, those containing, as a primary amino acid sequence, all or part of the amino acid sequence of Hsp90, including altered sequences in which functionally equivalent amino acid residues are substituted for residues within the sequence resulting in a silent change. For example, one or more amino acid residues within the sequence can be substituted by another amino acid of a similar polarity that acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The Hsp90 derivatives and analogs can be analyzed by hydrophilicity analysis (Hopp and Woods, 1981, Proc. Natl. Acad. Sci. USA 78:3824–3828). A hydrophilicity profile can be used to identify the hydrophobic and hydrophilic regions of the proteins, and help predict their orientation in designing substrates for experimental manipulation, such as in binding experiments, antibody synthesis, etc. Secondary structural analysis can also be done to identify regions of Hsp90, or derivatives thereof, that assume specific structures (Chou and Fasman, 1974, Biochemistry 13:222–23). Manipulation, translation, secondary structure prediction, hydrophilicity and hydrophobicity profile predictions, open reading frame prediction and plotting, and determination of sequence homologies, etc., can be accomplished using computer software programs available in the art.

Other methods of structural analysis including but not limited to X-ray crystallography (Engstrom, 1974 Biochem. Exp. Biol. 11:7–13), mass spectroscopy and gas chromatography (Methods in Protein Science, J. Wiley and Sons, N.Y., 1997), and computer modeling (Fletterick and Zoller, eds., 1986, Computer Graphics and Molecular Modeling, In: Current Communications in Molecular Biology, Cold Spring Harbor Laboratory, Cold Spring Harbor Press, N.Y.) can also be employed to determine which residues to modify in producing a fragment or derivative or analog of a Hsp90 molecule.

5.2.1. RECOMBINANT EXPRESSION

Methods for recombinant production of Hsp90 and derivatives or fragments or homologs thereof for use in the screening methods of the present invention are well known to those skilled in the art. Nucleic acids encoding Hsp90, derivatives, fragments, and homologs thereof are known in the art. The nucleotide sequences encoding illustrative Drosophila and human Hsp90 molecules are known and are provided in FIGS. 1, 2 and 3 (SEQ ID NOS: 1, 3 and 5). Nucleic acids encoding Hsp90α and Hsp90β can be obtained by any method known in the art, e.g., by PCR amplification using synthetic primers hybridizable to the 3' and 5' ends of each sequence, and/or by cloning from a cDNA or genomic library using an oligonucleotide specific for each nucleotide sequence.

Homologs (e.g., nucleic acids encoding Hsp90 of species other than human) or other related sequences (e.g., paralogs) can be obtained by low, moderate or high stringency hybridization with all or a portion of the particular human sequence as a probe, using methods well known in the art for nucleic acid hybridization and cloning.

The encoded Hsp90 proteins, which are depicted in FIGS. 1, 2 and 3, respectively (SEQ ID NO:2, SEQ ID NO:4 and SEQ ID NO:6, respectively) can be obtained by methods well known in the art for protein purification and recombinant protein expression. For recombinant expression of one or more of the proteins, the nucleic acid containing all or a portion of the nucleotide sequence encoding the protein can be inserted into an appropriate expression vector, i.e., a vector that contains the necessary elements for the transcription and translation of the inserted protein coding sequence. The necessary transcriptional and translational signals can also be supplied by the native promoter of the Hsp90 genes, and/or their flanking regions.

A variety of host-vector systems may be utilized to express the protein coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In a preferred embodiment, Hsp90α is obtained by expressing the Hsp90α coding sequence. In yet another embodiment, a derivative, fragment or homolog of Hsp90β is recombinantly expressed.

Any method available in the art can be used for the insertion of DNA fragments into a vector to construct expression vectors containing a chimeric gene consisting of appropriate transcriptional/translational control signals and protein coding sequences. These methods may include in vitro recombinant DNA and synthetic techniques and in vivo recombinant techniques (genetic recombination). Expression of nucleic acid sequences encoding Hsp90, or a derivative, fragment or homolog thereof, may be regulated by a second nucleic acid sequence so that the gene or fragment thereof is expressed in a host transformed with the recombinant DNA molecule(s). For example, expression of the proteins may be controlled by any promoter/enhancer known in the art. In a specific embodiment, the promoter is not native to the gene for Hsp90. Promoters that may be used include but are not limited to the SV40 early promoter (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. USA 78:1441–1445), the regulatory sequences of the metallothionein gene (Brinster et al., 1982, Nature 296:39–42); prokaryotic expression vectors such as the β-lactamase promoter (Villa-Kamaroff et al., 1978, Proc. Natl. Acad. Sci. USA 75:3727–3731) or the tac promoter (DeBoer et al., 1983, Proc. Natl. Acad. Sci. USA 80:21–25; Gilbert et al., 1980, Scientific American 242:79–94); plant expression vectors comprising the nopaline synthetase promoter (Herrar-Estrella et al., 1984, Nature 303:209–213) or the cauliflower mosaic virus 35S RNA promoter (Garder et al., 1981, Nucleic Acids Res. 9:2871), and the promoter of the photosynthetic enzyme ribulose bisphosphate carboxylase (Herrera-Estrella et al., 1984, Nature 310:115–120); promoter elements from yeast and other fungi such as the Gal4 promoter (Johnston et al., 1987, Microbiol. Rev. 51:458–476), the alcohol dehydrogenase promoter (Schibler et al., 1987, Annual Review Genetics 21:237–257), the phosphoglycerol kinase promoter (Struhl et al., 1995, Annual Review Genetics 29:651–674–257; Guarente 1987, Annual Review Genetics 21:425–452), the alkaline phosphatase promoter (Struhl et al., 1995, Annual Review Genetics 29:651–674–257; Guarente 1987, Annual Review Genetics 21:425–452), and the following animal transcriptional control regions that exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald 1987, Hepatology 7:425–515); insulin gene control region which is active in pancreatic beta cells (Hanahan et al., 1985, Nature 315:115–122), immunoglobulin gene control region which is active in lymphoid cells (Grosschedl et al., 1984, Cell 38:647–658; Adams et al., 1985, Nature 318:533–538; Alexander et al., 1987, Mol. Cell Biol. 7:1436–1444), mouse mammary tumor virus control region which is active in testicular, breast, lymphoid and mast cells (Leder et al., 1986, Cell 45:485–495), albumin gene control region which is active in liver (Pinckert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha-1 antitrypsin gene control region which is active in liver (Kelsey et al., 1987, Genes and Devel. 1:161–171), beta globin gene control region which is active in myeloid cells (Mogram et al., 1985, Nature 315:338–340; Kollias et al., 1986, Cell 46:89–94), myelin basic protein gene control region which is active in oligodendrocyte cells of the brain (Readhead et al., 1987, Cell 48:703–712), myosin light chain-2 gene control region which is active in skeletal muscle (Sani 1985, Nature 314:283–286), and gonadotrophic releasing hormone gene control region which is active in gonadotrophs of the hypothalamus (Mason et al., 1986, Science 234:1372–1378).

In a specific embodiment, a vector is used that comprises a promoter operably linked to the nucleic acid sequence encoding Hsp90, or a fragment, derivative or homolog thereof, one or more origins of replication, and optionally, one or more selectable markers (e.g., an antibiotic resistance gene).

In another specific embodiment, an expression vector containing the coding sequence, or a portion thereof, of Hsp90 is made by subcloning the gene sequence into the EcoRi restriction site of each of the three pGEX vectors (glutathione S-transferase expression vectors; Smith and Johnson, 1988, Gene 7:31–40). This allows for the expression of products in the correct reading frame.

Expression vectors containing the sequences of interest can be identified by three general approaches: (a) nucleic acid hybridization, (b) presence or absence of "marker" gene function, and (c) expression of the inserted sequences. In the first approach, Hsp90 sequences can be detected by nucleic acid hybridization to probes comprising sequences homologous and complementary to the inserted sequences. In the second approach, the recombinant vector/host system can be identified and selected based upon the presence or absence of certain "marker" functions (e.g. resistance to antibiotics, occlusion body formation in baculovirus, etc.) caused by insertion of the sequences of interest in the vector. For example, if a Hsp90 gene, or portion thereof, is inserted within the marker gene sequence of the vector, recombinants containing the Hsp90 fragment will be identified by the absence of the marker gene function (e.g., loss of beta-galactosidase activity). In the third approach, recombinant expression vectors can be identified by assaying for the Hsp90 expressed by the recombinant vector.

Once recombinant Hsp90 molecules are identified and isolated, several methods known in the art can be used to propagate them. Using a suitable host system and growth conditions, recombinant expression vectors can be propagated and amplified in quantity. As previously described, the expression vectors or derivatives which can be used include, but are not limited to, human or animal viruses such as vaccinia virus or adenovirus; insect viruses such as baculovirus, yeast vectors; bacteriophage vectors such as lambda phage; and plasmid and cosmid vectors.

In addition, a host cell strain may be chosen that modulates the expression of the inserted sequences, or modifies or processes the expressed proteins in the specific fashion desired. Expression from certain promoters can be elevated in the presence of certain inducers; thus expression of the genetically-engineered Hsp90 may be controlled. Furthermore, different host cells have characteristic and specific mechanisms for the translational and post-translational processing and modification (e.g., glycosylation, phosphorylation, etc.) of proteins. Appropriate cell lines or host systems can be chosen to ensure that the desired modification and processing of the foreign protein is achieved. For example, expression in a bacterial system can be used to produce an unglycosylated core protein, while expression in mammalian cells ensures "native" glycosylation of a heterologous protein. Furthermore, different vector/host expression systems may effect processing reactions to different extents.

In other specific embodiments, the Hsp90 protein or a fragment, homolog or derivative thereof, may be expressed as fusion or chimeric protein products comprising the protein, fragment, homolog, or derivative joined via a peptide bond to a heterologous protein sequence of a different protein. Such chimeric products can be made by ligating the appropriate nucleic acid sequences encoding the desired amino acids to each other by methods known in the art, in the proper coding frame, and expressing the chimeric products in a suitable host by methods commonly known in the art. Alternatively, such a chimeric product can be made by protein synthetic techniques, e.g., by use of a peptide synthesizer. Chimeric genes comprising portions of Hsp90 fused to any heterologous protein-encoding sequences may be constructed. A specific embodiment relates to a chimeric protein comprising a fragment of Hsp90 of at least six amino acids.

5.3. METHODS FOR IDENTIFYING MODULATORS OF Hsp90 FUNCTION

In one embodiment of the invention, methods are provided for the identification of modulators, e.g., inhibitors, antagonists, or agonists, of Hsp90 activity by detecting the ability of candidate molecules to effect an alteration of Hsp90 subcellular localization (qualitatively and/or quantitatively), and thus, perhaps its activity in chromosomal segregation. In one aspect of this embodiment of the invention, the method for identifying a modulator of Hsp90 activity comprises providing a cell with a candidate modulator molecule and detecting or measuring the amount of Hsp90 that co-purifies or co-localizes with the centrosome, in which a difference in the presence or amount of Hsp90 co-purifying or co-localizing to the centrosome compared to a cell not contacted with the candidate molecule indicates that the candidate molecule modulates Hsp90 activity. In another aspect of this embodiment of the invention, the method comprises providing a cell with a candidate modulator molecule and detecting or measuring aberrant mitotic figures, such as monopolar spindles, aneuploydies, chromosomal missegregation, or chromosome non-joinder, in which a difference in the presence of aberrant mitotic figures compared to a cell not contacted with the candidate molecule indicates that the molecule modulates Hsp90 activity.

A particular aspect of the present invention relates to identifying molecules that inhibit or promote Hsp90 localization to the centrosome.

Methods that can be used to carry out the foregoing are commonly known in the art and/or those methods disclosed in Section 5.1, supra. The cells used in the methods of this embodiment of the invention can either endogenously or recombinantly express Hsp90, or a fragment, derivative or analog thereof. Recombinant expression of Hsp90 is carried out by introducing Hsp90 encoding nucleic acids into expression vectors and subsequently introducing the vectors into a cell to express Hsp90 or simply introducing Hsp90 encoding nucleic acids into a cell for expression, as described in Section 5.2.1 or using procedures well known in the art. Nucleic acids encoding Hsp90 from a number of species have been cloned and sequenced and their expression is well known in the art. Illustrative examples of Hsp90 molecules are set forth in FIGS. 1, 2, and 3. Other illustrative examples of Hsp90 molecules are described in Krone et al., 1994, Biocehm. Biophys. Res. Commun. 204:746–752 (zebrafish Hsp90α); de Andrade et al., 1992, J. Clin. Microbiol. 30:330–335 (Leishmania); Meng et al., 1993, Biochem. Biophys. Res. Commun. 190:630–636 (chicken Hsp90β); McGuire et al., 1992, J. Steroid Biochem. Mol. Biol.

42:813–822 (rat Hsp90β); and Chen and Laszlo, 1995, direct submission to EMBL/GENBANK, Accession No. P46633 (chicken Hsp90α). Expression can be from expression vectors or intrachromosomal. In a specific embodiment, standard human cell lines, such as HeLa cells and human kidney 293 cells, are employed in the screening assays.

Any method known to those of skill in the art for the insertion of Hsp90-encoding DNA into a vector may be used to construct expression vectors for expressing Hsp90, including those methods described in Section 5.2, supra. In addition, a host cell strain may be chosen which modulates the expression of Hsp90, or modifies and processes the gene product in the specific fashion desired. Expression from certain promoters can be elevated in the presence of certain inducers; thus, expression of Hsp90 protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the Hsp90 protein expressed. For example, expression in a bacterial system can be used to produce an unglycosylated core protein product. Expression in yeast will produce a glycosylated product. Expression in mammalian cells can be used to ensure "native" glycosylation of a mammalian Hsp90 protein.

In a preferred embodiment, potential modulators of Hsp90 activity are initially identified by a genetic screen according to Cutforth and Rubin, 1994, Cell 77:1027–1036 ("Cutforth and Rubin"). In brief, the identification of a modulator of Hsp90 localization, and thus, its activity, can be identified according to the method of Cutforth and Rubin by mutagenizing wild type Drosophila males that carry appropriate markers and crossing the mutagenized males to females having a temperature sensitive allele of the seven-less gene ("ts sev"). The F1 flies are scored for those that have eyes that are either more rough or less rough compared to the mothers. Such F1 flies may carry a modifier (enhancer or suppressor) of either of the two genes (ts sev or Hsp90). These flies are then crossed with flies carrying balancer chromosomes such that the mutation may be isolated. This screen is possible since mutations in the Drosophila homolog of Hsp90 were recovered as enhancers of seven-less.

Once the mutant gene is isolated according to the method above, the mutant gene is tested according to the assays described in Section 5.1 to test whether its encoded protein has the ability to modulate the activity of Hsp90 by altering its subcellular localization to or amount of Hsp90 in the centrosome, i.e., whether the mutant gene is a modulator of Hsp90 activity. The fact that the mutant gene product can modulate Hsp90 function can also be assayed by contacting the cells with the mutant protein and determining whether Hsp90 purifies with or is localized to the centrosome in the same manner or amount, e.g., using spectroscopic or immunofluorescent analysis.

5.3.1. CANDIDATE MOLECULES

Any molecule known in the art can be tested for its ability to modulate (increase or decrease) Hsp90 activity as detected by a change in the subcellular localization of Hsp90 (or amount thereof). By way of example, a change in the localization can be detected by detecting a change in the amount of Hsp90 that purifies with or localizes to the centrosome. For identifying a molecule that modulates Hsp90 activity, candidate molecules can be directly provided to a cell expressing Hsp90, or, in the case of candidate proteins, can be provided by providing their encoding nucleic acids under conditions in which the nucleic acids are recombinantly expressed to produce the candidate proteins within the Hsp90 expressing cell.

This embodiment of the invention is well suited to screen chemical libraries for molecules which modulate, e.g., inhibit, antagonize, or agonize, Hsp90 activity by altering the amount of Hsp90 that purifies with or localizes to the centrosome. The chemical libraries can be peptide libraries, peptidomimetic libraries, chemically synthesized libraries, recombinant, e.g., phage display libraries, and in vitro translation-based libraries, other non-peptide synthetic organic libraries, etc.

Exemplary libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compound's composition. Also, in one example, a single plate position may have from 1–20 chemicals that can be screened by administration to a well containing the interactions of interest. Thus, if modulation is detected, smaller and smaller pools of interacting pairs can be assayed for the modulation activity. By such methods, many candidate molecules can be screened.

Many diversity libraries suitable for use are known in the art and can be used to provide compounds to be tested according to the present invention. Alternatively, libraries can be constructed using standard methods. Chemical (synthetic) libraries, recombinant expression libraries, or polysome-based libraries are exemplary types of libraries that can be used.

The libraries can be constrained or semirigid (having some degree of structural rigidity), or linear or nonconstrained. The library can be a cDNA or genomic expression library, random peptide expression library or a chemically synthesized random peptide library, or non-peptide library. Expression libraries are introduced into the cells in which the assay occurs, where the nucleic acids of the library are expressed to produce their encoded proteins.

In one embodiment, peptide libraries that can be used in the present invention may be libraries that are chemically synthesized in vitro. Examples of such libraries are given in Houghten et al., 1991, Nature 354:84–86, which describes mixtures of free hexapeptides in which the first and second residues in each peptide were individually and specifically defined; Lam et al., 1991, Nature 354:82–84, which describes a "one bead, one peptide" approach in which a solid phase split synthesis scheme produced a library of peptides in which each bead in the collection had immobilized thereon a single, random sequence of amino acid residues; Medynski, 1994, Bio/Technology 12:709–710, which describes split synthesis and T-bag synthesis methods; and Gallop et al., 1994, J. Medicinal Chemistry 37(9):1233–1251. Simply by way of other examples, a combinatorial library may be prepared for use, according to the methods of Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; or Salmon et al., 1993, Proc. Natl. Acad. Sci. USA 90:11708–11712. PCT Publication No. WO 93/20242 and Brenner and Lerner, 1992, Proc. Natl. Acad. Sci. USA 89:5381–5383 describe "encoded combinatorial chemical libraries," that contain oligonucleotide identifiers for each chemical polymer library member.

In a preferred embodiment, the library screened is a biological expression library that is a random peptide phage display library, where the random peptides are constrained (e.g., by virtue of having disulfide bonding).

Further, more general, structurally constrained, organic diversity (e.g., nonpeptide) libraries, can also be used. By way of example, a benzodiazepine library (see e.g., Bunin et al., 1994, Proc. Nati. Acad. Sci. USA 91:4708–4712) may be used.

Conformationally constrained libraries that can be used include but are not limited to those containing invariant cysteine residues which, in an oxidizing environment, cross-link by disulfide bonds to form cystines, modified peptides (e.g., incorporating fluorine, metals, isotopic labels, are phosphorylated, etc.), peptides containing one or more non-naturally occurring amino acids, non-peptide structures, and peptides containing a significant fraction of γ-carboxyglutamic acid.

Libraries of non-peptides, e.g., peptide derivatives (for example, that contain one or more non-naturally occurring amino acids) can also be used. One example of these are peptoid libraries (Simon et al., 1992, Proc. Natl. Acad. Sci. USA 89:9367–9371). Peptoids are polymers of non-natural amino acids that have naturally occurring side chains attached not to the alpha carbon but to the backbone amino nitrogen. Since peptoids are not easily degraded by human digestive enzymes, they are advantageously more easily adaptable to drug use. Another example of a library that can be used, in which the amide functionalities in peptides have been permethylated to generate a chemically transformed combinatorial library, is described by Ostresh et al., 1994, Proc. Natl. Acad. Sci. USA 91:11138–11142).

The members of the peptide libraries that can be screened according to the invention are not limited to containing the 20 naturally occurring amino acids. In particular, chemically synthesized libraries and polysome based libraries allow the use of amino acids in addition to the 20 naturally occurring amino acids (by their inclusion in the precursor pool of amino acids used in library production). In specific embodiments, the library members contain one or more non-natural or non-classical amino acids or cyclic peptides. Non-classical amino acids include but are not limited to the D-isomers of the common amino acids, α-amino isobutyric acid, 4-aminobutyric acid, Abu, 2-amino butyric acid; γAbu, ε-Ahx, 6-amino hexanoic acid; Aib, 2-amino isobutyric acid; 3-amino propionic acid; ornithine; norleucine; norvaline, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, Nα-methyl amino acids, fluoro-amino acids and amino acid analogs in general. Furthermore, the amino acid can be D (dextrorotary) or L (levorotary).

In a specific embodiment, fragments and/or analogs of Hsp90, especially peptidomimetics, are screened for activity as competitive or non-competitive inhibitors of Hsp90 centrosomal localization.

In another embodiment of the present invention, combinatorial chemistry can be used to identify modulators of Hsp90. Combinatorial chemistry is capable of creating libraries containing hundreds of thousands of compounds, many of which may be structurally similar. While high throughput screening programs are capable of screening these vast libraries for affinity for known targets, new approaches have been developed that achieve libraries of smaller dimension but which provide maximum chemical diversity. (See e.g., Matter, 1997, Journal of Medicinal Chemistry 40:1219–1229).

One method of combinatorial chemistry, affinity fingerprinting, has previously been used to test a discrete library of small molecules for binding affinities for a defined panel of proteins. The fingerprints obtained by the screen are used to predict the affinity of the individual library members for other proteins or receptors of interest (in the instant invention, Hsp90.) The fingerprints are compared with fingerprints obtained from other compounds known to react with the protein of interest to predict whether the library compound might similarly react. For example, rather than testing every ligand in a large library for interaction with Hsp90, only those ligands having a fingerprint similar to other compounds known to have that activity could be tested. (See, e.g., Kauvar et al., 1995, Chemistry and Biology 2:107–118; Kauvar, 1995, Affinity fingerprinting, Pharmaceutical Manufacturing International. 8:25–28; and Kauvar, Toxic-Chemical Detection by Pattern Recognition in New Frontiers in Agrochemical Immunoassay, D. Kurtz. L. Stanker and J. H. Skerritt. Editors, 1995, AOAC: Washington, D.C., 305-312).

Kay et al., 1993, Gene 128:59–65 (Kay) discloses a method of constructing peptide libraries that encode peptides of totally random sequence that are longer than those of any prior conventional libraries. The libraries disclosed in Kay encode totally synthetic random peptides of greater than about 20 amino acids in length. Such libraries can be advantageously screened to identify Hsp90 modulators. (See also U.S. Pat. No. 5,498,538 dated Mar. 12, 1996; and PCT Publication No. WO 94/18318 dated Aug. 18, 1994).

A comprehensive review of various types of peptide libraries can be found in Gallop et al., 1994, J. Med. Chem. 37:1233–1251.

5.4. DIAGNOSTIC, PROGNOSTIC, AND SCREENING USES OF Hsp90 LOCALIZATION

Centrosomal localization of Hsp90 is important in mitosis and fidelity of chromosomal segregation, and thus has diagnostic utility. Further, definition of particular groups of patients with aberrant localization of Hsp90 can lead to new nosological classifications of diseases, furthering diagnostic ability.

Detecting centrosomal localization of Hsp90 may be used in prognosis, to follow the course of a disease state, to follow a therapeutic response, etc.

Hsp90 and a derivative, analog or subsequence thereof, Hsp90 nucleic acids (and sequences complementary thereto), and anti-Hsp90 antibodies, are useful in diagnostics. The foregoing molecules can be used in assays, such as immunoassays, to detect, prognose, diagnose, or monitor various conditions, diseases, and disorders characterized by aberrant non-centrosomal localization of Hsp90, or monitor the treatment of such various conditions, diseases, and disorders. Other assay for detecting Hsp90 localization are described in Section 5.1, supra.

In particular, such an immunoassay is carried out by a method comprising contacting a sample derived from a patient with an anti-Hsp90 antibody under conditions such that immunospecific binding can occur, and detecting or measuring the amount of any immunospecific binding by the Hsp90 antibody that co-localizes with the centrosome. In a specific aspect, such binding of antibody, in tissue sections, can be used to detect aberrant Hsp90 localization. "Aberrant localization" is meant as non-centrosomal localization or less centrosomal localization relative to that present, or a standard level representing that present, in an analogous sample from a portion or fluid of the body, or from a subject not having a disorder.

The immunoassays which can be used include but are not limited to competitive and non-competitive assay systems using techniques such as Western blots, radioimmunoassays, ELISA (enzyme linked immunosorbent assay), "sandwich" immunoassays, immunoprecipitating assays, precipitin reactions, gel diffusion precipitin reactions, immunodiffusion assays, agglutination assays, complement-fixation assays, immunoradiometric assays, fluorescent immunoassays, protein A immunoassays, to name but a few known in the art. In a preferred embodiment, Hsp90 localization is assayed by immunofluorescence. In another preferred embodiment, centrosomes and the constituent proteins are isolated by any method known in the art and then subject to mass spectroscopy analysis to assay for the presence of Hsp90 at the centrosome.

In specific embodiments, diseases and disorders involving or characterized by aberrant localization of a Hsp90 can be diagnosed, or its suspected presence can be screened for, or a predisposition to develop such disorders can be detected, by detecting aberrant localization of Hsp90.

Assays well known in the art (e.g., assays described above such as immunoassays, those described in Sections 5.1 and 6 of this application, etc.) can be used to determine whether Hsp90 localization is altered in samples from patients suffering from a particular disease or disorder, or having a predisposition to develop such a disease or disorder, as compared to samples from subjects not having such a disease or disorder, or having a predisposition to develop such a disease or disorder.

Accordingly, in a specific embodiment of the present invention, diseases and disorders in which Hsp90 does not localize to the centrosome can be diagnosed, or their suspected presence can be screened for, or a predisposition to develop such disorders can be detected, by detecting whether Hsp90 is localized to the centrosome.

In the event that non-centrosomal localization of Hsp90 is determined to be relevant to patients suffering from a particular disease or disorder, or having a predisposition to develop such a disease or disorder, then the particular disease or disorder or predisposition for a disease or disorder can be diagnosed, have its prognosis determined, be screened for, or be monitored by detecting whether Hsp90 is localized to the centrosome.

Accordingly, in a specific embodiment of the invention, diseases and disorders in which Hsp90 does not localize to the centrosome can be diagnosed, or their suspected presence can be screened for, or a predisposition to develop such disorders can be detected, by detecting whether Hsp90 is localized to the centrosome.

The use of detection techniques, especially those involving antibodies against Hsp90, provides a method of detecting specific cells in which Hsp90 is no longer localized to the centrosome.

Kits for diagnostic use are also provided in the present invention, that comprise in one or more containers an anti-Hsp90 antibody, and, optionally, a labeled binding partner to the antibody. Alternatively, the anti-Hsp90 complex antibody can be labeled with a detectable marker, e.g., a chemiluminescent, enzymatic, fluorescent, or radioactive moiety. A kit is also provided that comprises in one or more containers an antibody specific for centrosomin, a previously characterized Drosophila centrosomal protein. A kit can optionally further comprise in a container cells in which Hsp90 is localized to the centrosome, e.g., for use as a standard or control.

The following series of examples are presented by way of illustration and not by way of limitation on the scope of the present invention.

6. EXAMPLE

The precise molecular composition of Drosophila centrosomes is undefined and only a few proteins are known to govern its duplication and function in microtubule nucleation. Using mass spectrometry and immuno-isolation methods to characterize the molecular composition of Drosophila centrosomes, the identification of protein components of the centrosome that had not previously been identified was realized. One such protein component is the heat shock protein Hsp83, a member of the Hsp90 family of proteins (a homolog of human Hsp90) and referred to as Hsp90 herein. As demonstrated below, Hsp90 is localized to the centrosome throughout the cell cycle, is conserved as a centrosome component from Drosophila to human, and is required for proper mitosis and fidelity of chromosome segregation.

6.1. Hsp90 IS LOCALIZED TO THE CENTROSOME

Centrosomes were isolated by homogenization from Drosophila embryos aged between 0 to 3.5 hours, cellular debris was removed, and density gradient centrifugation according to Moritz et al., 1995, J. Cell. Biol. 130:1149–1159 was performed to obtain a crude preparation of centrosomes. The "crude" centrosomes were further purified using an immuno-isolation protocol described in Lange et al., 1995, J. Cell Biol. 130:919–927. Briefly, sucrose fractions enriched in centrosomes as assayed by fluorescence microscopy were diluted 1:1 with PBS containing 0.1% BSA, a proteinase inhibitor mix containing Pepstatine A, Leupeptine, Aprotinin and Pefabloc and 5 $\mu$g/ml DNase and incubated with anti-$\gamma$-tubulin antibody RB 1011 originally described in Tavosanis et al., 1997, EMBO J. 16:1809–1819 for 1 hour at room temperature. The incubated mixture was overlaid onto a gradient of 70%, 55% and 35% sucrose (w/v) in a buffer of 80 mM PIPES, pH 6.8, 1 mM EGTA, and 1 mM MgCl$_2$, and centrifuged for 1.5 hour at 32,000 rpm in a Beckman SW40 rotor at 4° C.

Centrosome containing fractions were removed with a syringe and diluted 1:1 with PBS containing 0.2% BSA, the proteinase inhibitor mix containing Pepstatine A, Leupeptine, Aprotinin and Pefabloc and 5 $\mu$g/ml DNase. The sample was then incubated with 9.4×10$^8$ M-280 magnetic beads coated with anti-rabbit immunoglobulin obtained from Dynal (Lake Success, New York) for 1 hour at room temperature under gentle rotation. The magnetic beads carrying centrosomes were recovered with a magnetic collector and washed gently 3 times with PBS containing 0.1% BSA and 0.5% Triton X-100. A final washing step with PBS containing 0.5% Triton X-100 was performed and the isolated beads were analyzed by immunofluorescence microscopy, electron microscopy, SDS-PAGE gel analysis, and Western blot analysis. The preimmune serum of the Rb1011 rabbit was used as a control for the specificity of this isolation protocol.

The abundance of centrosomes coating the magnetic beads was confirmed by confocal laser scanning immunofluorescence microscopy using anti-$\gamma$-tubulin antibody according to the method of Lange et al., 1995, J. Cell Biol.

130:919–927 and demonstrated that γ-tubulin localization is specific to the centrosome and not localized on any other part of the magnetic bead. This evidences that centrosomal structures were isolated rather than soluble protein complexes containing γ-tubulin.

SDS-PAGE analysis of the proteins bound to the magnetic beads was performed by solubilizing the beads in 2×SDS sample buffer at 95° C. for two minutes, the magnetic beads were centrifuged and the supernatant applied to the well of a 10% SDS-PAGE gel. A complex pattern of about 20 distinct bands was visible when the gel was stained with coomassie blue, and about 50 distinct bands when the gel was stained with silver stain. The protein profile of this preparation is considerably different from the SDS-PAGE pattern of the total embryo homogenate and the intermediate centrosome enriched fraction (FIG. 4). Western blot analysis of these fractions with several antibodies raised against well characterized centrosomal and non-centrosomal proteins shows that the immuno-adsorbed fractions are a highly enriched centrosome preparation. Bands of interest were excised from the gel and in-gel digested with trypsin. A 0.3 µl portion of the supernatant was subjected to high mass accuracy peptide mass mapping on a Bruker REFLEX MALDI time of flight mass spectrometer using the fast evaporation technique for matrix preparation described by Jensen et al., 1997, Anal. Chem. 69:4741–4750. A nonredundant database containing more than 300,000 entries was searched using the Peptide Search algorithm and the approximately 90 kDa-sized band was identified as IIS83-DROME HEAT SHOCK PROTEIN, the Drosophila homolog of human Hsp90.

Other bands of interest were cut out of the gel and were analyzed as above. For the 140 kDa band, the isolated protein was first desalted on a Poros R2 column and then eluted directly into a nano-electrospray needle in accordance with the method disclosed in Wilm et al., 1996, Nature 379:466–469. Tandem experiments were carried out on a triple quadrupole mass spectrometer (API III, PE-Sciex, Ontario, Canada) and the sequences of six tryptic peptides were obtained, which unambiguously identified the protein as CCN_DROME CENTROSOMIN, a previously described centrosomal protein (Li and Kaufmann, 1996, Cell 85:585–596). The six tryptic peptide sequences obtained were QTLVENELATR (SEQ ID NO:7); IYFLEEGQPGAR (SEQ ID NO:8); LADDQQNSAVIGQLR (SEQ ID NO:9); IAQLEEQIAQKDER (SEQ ID NO:10); AINEALTADLQAIGSHEEER (SEQ ID NO: 11); and DLGAQLADKICELQEAQEK (SEQ ID NO:12).

6.2 IMMUNOFLUORESCENCE STAINING OF Hsp90

To rule out a possible artifactual association of Hsp90 with the centrosome during the course of centrosome purification, the subcellular localization of Hsp90 in whole mount Drosophila embryos was studied by immunofluorescent confocal microscopy according to the method described in Pisano et al., 1993, Genetics 133:569–579. Hsp90 was found to be distinctively associated to the centrosome before and after cellularization, i.e., before and after cell membranes are formed during Drosophila development. The fact that Hsp90 remains associated to the centrosome throughout the centrosome purification procedure suggests a strong non-microtubule-dependent association with this organelle during embryogenesis. To determine whether Hsp90 remained in the centrosome beyond embryonic stages, mature Drosophila testes was studied.

Drosophila testis tissue was prepared from pupae and was stained with anti-α-tubulin antibody obtained from Amersham (Braunschweig, Germany) and anti-Hsp90 antibody obtained from Dianova, Hamburg, Germany, according to the method described by Pisano et al., 1993, Genetics 133:569–579. Hsp90 was found in the centrosomes throughout spermatogenesis, including the mitotic gonial cells and meiotic spermatocytes. After meiosis, Hsp90 was also shown to co-localize with the basal bodies of elongating spermatids. Moreover, Hsp90 was detected at a very precise location of the basal body area of the proximal end of the early axoneme in early sperm stages. Hsp90 was also present at the spindle poles of mitotic and meiotic cells in the testis. This striking and consistent localization of Hsp90 to the centrosome throughout the cell cycle and in different developmental stages identifies Hsp90 as a core centrosomal protein in Drosophila throughout development.

Also, four mammalian cells were stained according to the protocol of MacRae et al., 1990, Mol. Reprod. and Develop. 25:384–392 with an anti-α-tubulin and three anti-Hsp90 antibodies, 16F1 (Lai et al., 1984, Mol. Cell Biol. 4:2802–2810), AC88 (Riehl et al., 1985, Biochemistry 24:6586–6591), and 771 (Perdew et al., 1993, Exp. Cell Res. 209:350–356). The mammalian cell lines employed were NIH 3T3 cells, a primary chicken cell line (CES), a mouse embryo fibroblast cell line (EFWT), and primary hippocampal neurons obtained from rat embryos. As seen in Drosphila, a fraction of Hsp90 was localized to the centrosome in interphase and mitotic cells in all the cell lines tested. This localization was more prominent when the bulk of Hsp90, which is in the cytoplasm, had been partially extracted prior to fixation, but could also be observed without extraction. Like in purified Drosophila centrosomes, the centrosomal localization of Hsp90 in mammalian cells is maintained after extraction with nonionic detergents.

The fact that Hsp90 remains associated with the centrosomes throughout the lengthy centrosome isolation protocol points to its strong association with the centrosome. Moreover, the striking and consistent localization of Hsp90 to the centrosome throughout the cell cycle and in different developmental stages clearly demonstrates that Hsp90 is a core protein of the centrosome in both Drosophila and humans, and indicates an important role for Hsp90 in microtubule-related function.

6.3 GENETIC ANALYSIS

The centrosomal localization of a protein may not necessarily reflect a centrosomal role (Kals and Schliwa, 1993, Trends Cell Biol. 3:118–128). Therefore, it was decided to determine whether Hsp90 performs a yet unknown centrosomal function. To test this hypothesis a combined genetic and a pharmacological approach was followed that included the cytological characterization of the effects brought about by mutation of the Drosophila Hsp90 gene, and by treatment of mammalian tissue culture cells with geldanamycin, a potent Hsp90 inhibitor (see Section 6.4).

For the genetic analysis, attention was focused on two trans-heterozygous combinations, $hsp83^{582}/hsp83^{9J1}$ and $hsp83^{582}/hsp83^{13F3}$, of mutant allele which allow for larval and early pupae development (van der Straten, 1997, EMBO J. 16:1961–1969). Together with well arranged, indistinguishable from wild type, mitotic figures, as expected by a leaky mutant combination, the larval brains of these mutants revealed numerous aneuploid and polyploid cells as well as disorganized anaphase figures. Thus, chromosome segregation is severely impaired in Hsp90 mutant individuals, even in cases like these two allelic combinations which are not completely deficient for Hsp90 function. Recently, it was reported that a reduction in Hsp90 function affects microtubules at all stages of Drosophila spermatogenesis as well as in yeast cells (Yue et al., 1999, Genetics 151:1065–1079, "Yue"). Yue also showed that these effects are unlikely to be due to a direct role of Hsp90 in microtubule dynamics. The observations made herein indicate that these effects are due to abnormal centrosome function, and thus, the cause of this effect may be a failure in microtubule organization brought about by the reduced levels of functional Hsp90.

6.4 GELDANAMYCIN TREATMENT

Geldanamycin specifically interferes with the function of Hsp90 by binding to the ATP binding site of Hsp90 (Prodromou et al., 1997, Cell 90:65–75; Stebbins et al., 1997, Cell 89:239–250). Hela and human epithelial kidney 293 cells were treated with 1 µg/ml geldanamycin for times ranging from 0 to 32 hours (15 minutes, 30 minutes, 1 hour, 5 hours, 15 hours, 20 hours and 30 hours) and were stained with anti-α-tubulin, anti-γ-tubulin and anti-Hsp90 antibodies.

Geldanamycin treatment did not result in any noticeable effect either on the microtubule cytoskeleton nor on the morphology and number of centrosomes in interphase cells, as judged by immunofluorescence microscopy with antibodies against α- and γ-tubulin. However, aberrant mitotic spindles were detected from as early as 1 hour of treatment with geldanamycin. More than 50% of the mitotic figures produced in the presence of the drug after 20 hours of treatment contained aberrant mitotic figures in which the centrosomes, the spindles, and the distribution of chromatin were severely disrupted. In most cases, the two centrosomes of a cell were of very different sizes and had abnormal shapes as revealed by immunostaining with antibodies against γ-tubulin. The spindles of these cells were rather asymmetric, with unequal amounts of microtubules in each hemi-spindle and spindle poles very often detached from the centrosome. The aster microtubules which are organized around the centrosome were also abnormal in number and distribution. Typically, the chromosomes were seen condensed and aligned in a metaphase plate and no anaphases were observed, suggesting a block in the metaphase-anaphase transition. About 50% of the cells contained misaligned chromosomes. Thus, while the centrosome and the cytoskeleton of interphase cells were insensitive to geldanamycin, mitotic centrosomes cannot be properly formed in the presence of geldanamycin. This specific effect on mitotic centrosomes, which have to grow significantly at the onset of mitosis and are much more sensitive than interphase centrosomes to geldanamycin, indicates that Hsp90 plays a role in centrosome organization. Therefore, notwithstanding the possible contribution of other non-centrosomal functions of Hsp90 to some of these phenotypes, it is clear that the inhibition of the function of Hsp90 results in abnormalities in centrosome structure.

6.5 CONCLUSION

In summary, Hsp90 is an abundant, ubiquitous protein that has been shown to be involved in many cellular processes. Nevertheless, it is generally accepted, that the major role (or roles) of this essential protein were unknown. The present inventors have found that Hsp90 is a core centrosomal component that is required for centrosome function in Drosophila and vertebrate cells. The present inventors have also shown Hsp90 to be present in specialized microtubule organizing centers, such as the sperm basal body. It is concluded that insuring proper centrosome function and all the processes which depend upon a functional microtubule organizing center is one of the major cellular functions of Hsp90.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications and patent applications are cited herein, the disclosures of which are incorporated by reference in their entireties.

We claim:

1. A method of identifying a molecule that alters the centrosomal location of Hsp90 in a cell comprising the following steps in the order stated:
   (a) contacting the cell with one or more candidate molecules; and
   (b) measuring the amount of Hsp90 molecules localized to the centrosome in the cell,
   wherein an increase or decrease in the amount of Hsp90 localized to the centrosome relative to said amount in a cell not so contacted with the one or more candidate molecules indicates that the candidate molecules alter the centrosomal localization of Hsp90.

2. A method of identifying a molecule that alters the centrosomal location of Hsp90 in a cell comprising the following steps in the order stated:
   (a) recombinantly expressing within the cell one or more candidate molecules; and
   (b) measuring the amount of Hsp90 molecules localized to the centrosome in the cell,
   wherein an increase or decrease in the amount of Hsp90 localized to the centrosome relative to said amount in a cell in which the one or more candidate molecules were not so expressed indicates that the candidate molecules alter the centrosomal localization of Hsp90.

3. The method according to claim 1 or 2 wherein step (b) comprises contacting the cell with an antibody to Hsp90 or an Hsp90 binding region of said antibody, and a fluorescently labeled binding partner of said antibody under conditions conducive to immunospecific binding.

4. The method according to claim 1 or 2 wherein step (b) comprises contacting the cell with a fluorescently labeled antibody to Hsp90 or an Hsp90 binding region of said antibody under conditions conducive to immunospecific binding.

5. The method according to claim 1 or 2 wherein step (b) comprises sequencing by mass spectroscopy a portion of a centrosomal protein isolated from the cell.

6. The method according to claim 1 or 2 wherein the cell is a cultured cell.

7. A method of identifying a molecule that affects Hsp90 function in a cell comprising the following steps in the order stated:
   (a) contacting the cell with one or more candidate molecules; and
   (b) detecting or measuring altered centrosomal or chromosomal structure or function,
   wherein an alteration of centrosomal or chromosomal structure or function relative to said structure or function in a cell not so contacted with the one or more candidate molecules indicates that the candidate molecules affects Hsp90 function.

8. A method of identifying a molecule that affects Hsp90 function in a cell comprising the following steps in the order stated:
   (a) recombinantly expressing within the cell one or more candidate molecules; and
   (b) detecting or measuring altered centrosomal or chromosomal structure or function,
   wherein an alteration of centrosomal or chromosomal structure or function relative to said structure or function in a cell in which the one or more candidate molecules were not so expressed indicates that the candidate molecules affects Hsp90 function.

9. The method according to claim 7 or 8 in which altered centrosomal or chromosomal structure or function is evidenced by an aberrant mitotic figure.

10. The method according to claim 9 in which the aberrant mitotic figure is selected from the group consisting of monopolar spindles, aneuploidies, chromosomal missegregation, and chromosome non-joinder.

11. A method of identifying a molecule that alters the centrosomal location of Hsp90 in a cell comprising the following steps in the order stated:
    (a) microinjecting into the cell one or more candidate molecules; and
    (b) measuring the amount of Hsp90 molecules localized to the centrosome in the cell,
    wherein an increase or decrease in the amount of Hsp90 localized to the centrosome relative to said amount in a cell not so microinjected with the one or more candidate molecules indicates that the candidate molecules alter the centrosomal localization of Hsp90.

12. A method for screening for a molecule that modulates directly or indirectly Hsp90 function comprising the following steps in the order stated:
    (a) contacting a cell expressing Hsp90 with one or more candidate molecules; and
    (b) detecting the levels of Hsp90 localized to the centrosome in said cell relative to said levels in a cell not contacted with said candidate molecules,
    wherein a higher or lower level of Hsp90 localization to the centrosome in the presence of said candidate molecules indicates that the molecules modulate the function of Hsp90.

13. A method for screening for a molecule that modulates directly or indirectly Hsp90 function comprising the following steps in the order stated:
    (a) recombinantly expressing one or more candidate molecules within a cell expressing Hsp90; and
    (b) detecting the levels of Hsp90 localized to the centrosome in said cell relative to said levels in a cell in which candidate molecules were not so expressed, wherein a higher or lower level of Hsp90 localization to the centrosome in the presence of said candidate molecules indicates that the molecules modulate the function of Hsp90.

14. The method according to claim 12 or 13 wherein the candidate molecule decreases the amount of Hsp90 localization to the centrosome, thereby being a candidate inhibitor of Hsp90 function.

15. The method according to claim 12 or 13 wherein the candidate molecule increases the amount of Hsp90 localization to the centrosome, thereby being a candidate agonist of Hsp90 function.

16. The method according to claim 12 or 13 wherein the candidate molecules are derived from a constrained random peptide library.

17. The method according to claim 12 or 13 wherein Hsp90 localization to the centrosome is detected by a method comprising contacting the cell with a molecule that binds to Hsp90 and a molecule that binds to a centrosome-specific protein other than Hsp90 under conditions conducive to binding, and detecting any binding of the molecules to the same subcellular location that occurs.

18. The method according to claim 12 or 13 wherein step (b) comprises contacting the cell with a fluorescently labeled antibody to Hsp90 or an Hsp90 binding region of the antibody under conditions conducive to immunospecific binding.

* * * * *

SEQUENCE LISTING

<160> NUMBER OF SEQ ID NOS: 12

<210> SEQ ID NO 1
<211> LENGTH: 5024
<212> TYPE: DNA
<213> ORGANISM: Drosophila melanogaster
<220> FEATURE:
<221> NAME/KEY: CDS
<222> LOCATION: (2155)..(4305)

<400> SEQUENCE: 1

```
ggatccttaa ccgggaactt gaagaagtgc atattggggt tgcggctaga acccaccgga      60
caatcacgaa aacaacactt agtgccgccc atttgtttaa atataagcaa acaacttta      120 tgttattagt ggtggaagtg ttagcgtcag ctggtgatat cgatgggagg catcgataac     180
agaattgacc gaaaccaaat gatcgatatg acacttctta attaatgaga gatttttac     240 ttgactgggc atgtagcagg ttttgcacag aagcaattat tttccggaat gtgaaatgtc     300 tgcttttag ctaattacaa caaaaacttt ccaattttg ttccccaaac ccactcaagt      360
```

-continued

```
gatttcaaat tttaccgtcc gcttaaaatg aactagttc caggaacc agcttgcacc      420
accaagtctc tgaaactctg gaaatatcga tagtctggtg gagaaaagta ttcataaata    480
taaataaaaa ttaacaggtc ataagctgat ttgtttatta tttactgtta aaacaagtaa    540
aataatattg ggaacaatta aattttccat tttcctaatt acagtataag cctagtgggc    600
gttttgatat ccaattgtaa tgttttaagc aatcccagtg ggctttgctc aatcgttcgg    660
accacttaga cgaatttcca ccaaacttag ttcagtataa ttttttgaatt cgcccgcaca   720
ggttgcgcac ttttcgaccg tatcacaaca ctgatctacc ctagtattca caggaagttg   780
catccctggc atccagaagc tctagaagt ttctagagac ttccagttcg ggtcgggttt    840
ttctataaaa gcagacgcgc ggcgtttgcc ggttcgagtc ttgaaaaaaa tttcgtacgg   900
tgtgcgtcgt aacaacaagc agcgtctgaa aagttttgtg aatttccaat tctatacaaa   960
gcaaagtgaa aatatctgta tttttaccttt tattctgtga atagaacgaa aaacatacat  1020
acaaggtgag taatgcaaat taaaagaaaa gagtgaatag tttcagtggc tatggccaaa  1080
atgtgcattt tgcgtggtcc tgtgcatctc gaatgttctt gacccaaatg tgagatattg  1140
attttaaatt tctaggagcc aagtttaaga attttttta tttaattaga ggtggcaacg    1200
tgcaaattaa ctcaaaattc cggtttcttt tattttttgt cgcttggacg catcttccag   1260
aggtttctat gctttagcat gaattaaaca tcgtgccaaa taggccttt aattatatat    1320
tactgtcctt tatttacaat tacatgtggt ttctagaata caagattaat ttttgtttaa   1380
ttaatgcaat ggtcttttag cgctaaatcg aattatgccg ctctttttag gggtgacaat   1440
gcgcaaatca catttgccgc tcgagaatgt tctagaggtt tctatgcttt agcatgaatt   1500
aaacagcgtg ccaaataggc ttttttaatta taaattactg tccttcattt acatttacac   1560
gtgctttctt tgcattccca ttttaaattg cacatgccgc atacgcacat gcacgcccat    1620
gactaatact ttcaagtaaa aatgtggcgt cagtaagcaa attctgttaa atcggttttt   1680
taatcctatt tgctctattt taattggttg gttgctacta gcaacttgct aggcgaatta   1740
gttttccttt ggcttctaga tgcttccaca aacttccttg gtgaagtacg aattttcaat   1800
gcaatgctca ctcacacaga cacgagtttg cacacagcag gggtagaaaa attatcaacc   1860
gacccaattt gcataattat atttaaatat ttaaatttaa aacattattt tgcaacttaa   1920
aatcaattct gttgcctaat tgaaattaaa attccatttt acgggttgca aagtgaatgc   1980
tataattttg accaccactg tacttgtata tgcgcatgtt aaatgaggca tgtgcaaaag   2040
agaaagaaag aaaaagaata aaaccggagc agctgctgaa aatgcagctg cttttcctta   2100
gtgttgaacc cacagactat aactaatcct aatgattttg taaatccatt gcag atg     2157
                                                              Met
                                                                1 cca gaa gaa gca gag acc ttt gca ttc cag gct gag att gct cag ctg    2205
Pro Glu Glu Ala Glu Thr Phe Ala Phe Gln Ala Glu Ile Ala Gln Leu
           5                  10                  15 atg tcc ctg atc atc aac aca ttc tac tcg aac aag gag att ttc ctg   2253
Met Ser Leu Ile Ile Asn Thr Phe Tyr Ser Asn Lys Glu Ile Phe Leu
         20                  25                  30 cgc gag ttg atc tcg aac gct tcc gat gcc ctg gac aag atc cgc tat   2301
Arg Glu Leu Ile Ser Asn Ala Ser Asp Ala Leu Asp Lys Ile Arg Tyr
     35                  40                  45 gag tcc ctt act gac ccc agc aag ctg gac tct ggc aag gag ctg tac   2349
Glu Ser Leu Thr Asp Pro Ser Lys Leu Asp Ser Gly Lys Glu Leu Tyr
 50                  55                  60                  65 atc aag ctg atc cct aac aag acg gct ggt act ctg acc atc att gat   2397
```

```
Ile Lys Leu Ile Pro Asn Lys Thr Ala Gly Thr Leu Thr Ile Ile Asp
             70                  75                  80 acc ggt atc ggt atg acc aag tcc gac ctg gtc aac aac ttg gga acc    2445
Thr Gly Ile Gly Met Thr Lys Ser Asp Leu Val Asn Asn Leu Gly Thr
             85                  90                  95 atc gcc aag tcc gga acc aag gcc ttc atg gag gct ctg cag gct ggt    2493
Ile Ala Lys Ser Gly Thr Lys Ala Phe Met Glu Ala Leu Gln Ala Gly
        100                 105                 110 gcc gac att tcc atg atc ggt cag ttc ggt gtg ggt ttc tac tcc gcc    2541
Ala Asp Ile Ser Met Ile Gly Gln Phe Gly Val Gly Phe Tyr Ser Ala
    115                 120                 125 tac ctg gtc gcc gac aag gtg act gtc acc tcc aag aac aac gat gac    2589
Tyr Leu Val Ala Asp Lys Val Thr Val Thr Ser Lys Asn Asn Asp Asp
130                 135                 140                 145 gag cag tac gtg tgg gag tcc tct gcc gga ggc tct ttc aca gtc cgt    2637
Glu Gln Tyr Val Trp Glu Ser Ser Ala Gly Gly Ser Phe Thr Val Arg
                150                 155                 160 gcc gac aac tct gag ccc ctg ggc cgt ggc acc aag atc gtg ctg tac    2685
Ala Asp Asn Ser Glu Pro Leu Gly Arg Gly Thr Lys Ile Val Leu Tyr
            165                 170                 175 atc aag gag gac cag acc gac tat ctg gag gag agc aag atc aag gag    2733
Ile Lys Glu Asp Gln Thr Asp Tyr Leu Glu Glu Ser Lys Ile Lys Glu
        180                 185                 190 att gtt aac aag cac tcc cag ttc att ggc tac ccc atc aag ctg ctc    2781
Ile Val Asn Lys His Ser Gln Phe Ile Gly Tyr Pro Ile Lys Leu Leu
    195                 200                 205 gta gag aag gag cgc gag aag gag gtc agc gac gat gag gct gat gat    2829
Val Glu Lys Glu Arg Glu Lys Glu Val Ser Asp Asp Glu Ala Asp Asp
210                 215                 220                 225 gag aag aag gaa ggt gat gag aag aag gag atg gag act gat gag ccc    2877
Glu Lys Lys Glu Gly Asp Glu Lys Lys Glu Met Glu Thr Asp Glu Pro
                230                 235                 240 aaa atc gag gat gtt ggc gag gat gag gat gcc gac aag aag gac aag    2925
Lys Ile Glu Asp Val Gly Glu Asp Glu Asp Ala Asp Lys Lys Asp Lys
            245                 250                 255 gat gcc aag aag aag aag acc atc aag gag aag tac act gag gat gag    2973
Asp Ala Lys Lys Lys Lys Thr Ile Lys Glu Lys Tyr Thr Glu Asp Glu
        260                 265                 270 gag ctg aac aag acc aag ccc atc tgg acc cgc aat ccc gat gat atc    3021
Glu Leu Asn Lys Thr Lys Pro Ile Trp Thr Arg Asn Pro Asp Asp Ile
    275                 280                 285 tcc cag gag gag tac ggc gag ttc tac aaa tcc ctg acc aac gac tgg    3069
Ser Gln Glu Glu Tyr Gly Glu Phe Tyr Lys Ser Leu Thr Asn Asp Trp
290                 295                 300                 305 gag gat cat ctg gcc gtc aag cac ttc tcc gtg gag ggt cag ctg gag    3117
Glu Asp His Leu Ala Val Lys His Phe Ser Val Glu Gly Gln Leu Glu
                310                 315                 320 ttc cgt gct ctg ctc ttc att ccc cgt cgc acg ccc ttc gat ctc ttt    3165
Phe Arg Ala Leu Leu Phe Ile Pro Arg Arg Thr Pro Phe Asp Leu Phe
            325                 330                 335 gag aac cag aag aag cgc aac aac atc aag ctg tac gtg cgt cgt gtc    3213
Glu Asn Gln Lys Lys Arg Asn Asn Ile Lys Leu Tyr Val Arg Arg Val
        340                 345                 350 ttc atc atg gac aac tgc gag gac ctc att cca gag tac ttg aac ttc    3261
Phe Ile Met Asp Asn Cys Glu Asp Leu Ile Pro Glu Tyr Leu Asn Phe
    355                 360                 365 atg aag ggt gtg gtc gac tcc gag gat ctg ccc ctc aac atc tca cgt    3309
Met Lys Gly Val Val Asp Ser Glu Asp Leu Pro Leu Asn Ile Ser Arg
370                 375                 380                 385
```

-continued

| | |
|---|---|
| gag atg ctg cag cag aac aag gtc cta aag gtg atc cgc aag aac ctg<br>Glu Met Leu Gln Gln Asn Lys Val Leu Lys Val Ile Arg Lys Asn Leu<br>            390                 395                 400 | 3357 |
| gtc aag aag acc atg gag ctg att gag gag ctc acc gag gac aag gag<br>Val Lys Lys Thr Met Glu Leu Ile Glu Glu Leu Thr Glu Asp Lys Glu<br>        405                 410                 415 | 3405 |
| aac tac aag aag ttc tat gac cag ttc agc aag aac ctg aag ctg ggt<br>Asn Tyr Lys Lys Phe Tyr Asp Gln Phe Ser Lys Asn Leu Lys Leu Gly<br>            420                 425                 430 | 3453 |
| gtg cac gag gac agc aac aac cgt gcc aag ttg gcc gac ttc ctt cgc<br>Val His Glu Asp Ser Asn Asn Arg Ala Lys Leu Ala Asp Phe Leu Arg<br>    435                 440                 445 | 3501 |
| ttc cac acc tct gcc tcc ggc gac gat ttc tgc tcc ctg gcc gac tac<br>Phe His Thr Ser Ala Ser Gly Asp Asp Phe Cys Ser Leu Ala Asp Tyr<br>450                 455                 460                 465 | 3549 |
| gtg tcg cgc atg aag gat aac cag aag cac gtg tac ttc atc act ggc<br>Val Ser Arg Met Lys Asp Asn Gln Lys His Val Tyr Phe Ile Thr Gly<br>            470                 475                 480 | 3597 |
| gag tcc aag gac cag gtc agc aac tct gcc ttc gtg gag cgc gtc aag<br>Glu Ser Lys Asp Gln Val Ser Asn Ser Ala Phe Val Glu Arg Val Lys<br>        485                 490                 495 | 3645 |
| gcc cgt ggc ttc gag gtg gtc tac atg acc gag ccc atc gat gag tat<br>Ala Arg Gly Phe Glu Val Val Tyr Met Thr Glu Pro Ile Asp Glu Tyr<br>            500                 505                 510 | 3693 |
| gtc atc cag cac ttg aag gag tac aag ggc aag cag ctg gtc tct gtc<br>Val Ile Gln His Leu Lys Glu Tyr Lys Gly Lys Gln Leu Val Ser Val<br>    515                 520                 525 | 3741 |
| acc aag gag ggt ctg gag ctg cct gag gat gag agc gag aag aag aag<br>Thr Lys Glu Gly Leu Glu Leu Pro Glu Asp Glu Ser Glu Lys Lys Lys<br>530                 535                 540                 545 | 3789 |
| cgc gag gag gac aag gcc aag ttc gag agc ctg tgc aag ctg atg aag<br>Arg Glu Glu Asp Lys Ala Lys Phe Glu Ser Leu Cys Lys Leu Met Lys<br>            550                 555                 560 | 3837 |
| tcc atc ctg gac aac aag gtc gag aag gtg gtg gtg tcc aac cgc ctg<br>Ser Ile Leu Asp Asn Lys Val Glu Lys Val Val Val Ser Asn Arg Leu<br>        565                 570                 575 | 3885 |
| gtg gat tcg ccc tgc tgc att gtc act tcg cag ttc ggc tgg tcc gct<br>Val Asp Ser Pro Cys Cys Ile Val Thr Ser Gln Phe Gly Trp Ser Ala<br>            580                 585                 590 | 3933 |
| aac atg gag cgc atc atg aag gcc cag gct ctg cgt gat acc gcc aca<br>Asn Met Glu Arg Ile Met Lys Ala Gln Ala Leu Arg Asp Thr Ala Thr<br>    595                 600                 605 | 3981 |
| atg ggc tac atg gcc ggc aag aag cag ctg gag atc aac ccc gat cac<br>Met Gly Tyr Met Ala Gly Lys Lys Gln Leu Glu Ile Asn Pro Asp His<br>610                 615                 620                 625 | 4029 |
| cca att gtg gag act ctc cgc cag aag gcc gat gcc gac aag aac gat<br>Pro Ile Val Glu Thr Leu Arg Gln Lys Ala Asp Ala Asp Lys Asn Asp<br>            630                 635                 640 | 4077 |
| aag gcc gtc aag gat ctg gtc atc ctg ctg ttc gag acc tct ctg ctg<br>Lys Ala Val Lys Asp Leu Val Ile Leu Leu Phe Glu Thr Ser Leu Leu<br>        645                 650                 655 | 4125 |
| tcc tct gga ttc tcg ctg gac agc ccc cag gtg cac gcc agc cgc atc<br>Ser Ser Gly Phe Ser Leu Asp Ser Pro Gln Val His Ala Ser Arg Ile<br>            660                 665                 670 | 4173 |
| tac cgc atg atc aag ctg ggc ttg gga atc gac gag gac gag cct atg<br>Tyr Arg Met Ile Lys Leu Gly Leu Gly Ile Asp Glu Asp Glu Pro Met<br>    675                 680                 685 | 4221 |
| act acc gac gat gcc cag agc gcc gga gat gcc ccc tcg ctg gtt gag<br>Thr Thr Asp Asp Ala Gln Ser Ala Gly Asp Ala Pro Ser Leu Val Glu<br>690                 695                 700                 705 | 4269 |

-continued

```
gac acc gag gac gct tcc cac atg gag gag gtc gat taagcgacca          4315
Asp Thr Glu Asp Ala Ser His Met Glu Glu Val Asp
            710                 715 gtcgaaacaa acaaccaaaa ttcattctat cactcgcatt cacatacaca atttacttgc   4375
gtttcgaact tttatactga gtttactacg gccgagttaa attttgtatt cattaacatt   4435
ttgccgcgtt ataagcgaca gacatacgct taactcataa aaaagcagga ataactcgtt   4495
aaatggttag gttctcacag aacattcaag agcagttgtc gttttaagaa cttataattt   4555
agaatccaag taatttatgt aaaaaactaa agactacata cgcgccctag ttggtagagc   4615
tatataaaga atcgagtata tatataatta aggtttgatg acccgatcga tgataaacat   4675
aaaaccaaat aaacaacaag caaatgtgtt ttaaaaatct aacttctgag cgagtattta   4735 ttgggggaa taaacaatct atgaatcgga ttctttgcgc agcagctgct caatggcctc    4795
caccgtggac actccgttgg ttatcattat tatcttgttt cgcgatcgag atcccttgtc   4855
caaagaaacg tcgctctttc gaagacctag aactttcgac agaaacttga ccagttcggc   4915
gttagcttct ccctcgctgg gcggagcggc gatttggacg cccactcctt caaagccaat   4975
tcctgtgatt ccgttctgct tagcccccgg cttggcaagg atttgtatg               5024
```

<210> SEQ ID NO 2
<211> LENGTH: 717
<212> TYPE: PRT
<213> ORGANISM: Drosophila melanogaster

<400> SEQUENCE: 2

```
Met Pro Glu Glu Ala Glu Thr Phe Ala Phe Gln Ala Glu Ile Ala Gln
 1               5                  10                  15

Leu Met Ser Leu Ile Ile Asn Thr Phe Tyr Ser Asn Lys Glu Ile Phe
            20                  25                  30

Leu Arg Glu Leu Ile Ser Asn Ala Ser Asp Ala Leu Asp Lys Ile Arg
        35                  40                  45

Tyr Glu Ser Leu Thr Asp Pro Ser Lys Leu Asp Ser Gly Lys Glu Leu
     50                  55                  60

Tyr Ile Lys Leu Ile Pro Asn Lys Thr Ala Gly Thr Leu Thr Ile Ile
 65                  70                  75                  80

Asp Thr Gly Ile Gly Met Thr Lys Ser Asp Leu Val Asn Asn Leu Gly
                85                  90                  95

Thr Ile Ala Lys Ser Gly Thr Lys Ala Phe Met Glu Ala Leu Gln Ala
            100                 105                 110

Gly Ala Asp Ile Ser Met Ile Gly Gln Phe Gly Val Gly Phe Tyr Ser
        115                 120                 125

Ala Tyr Leu Val Ala Asp Lys Val Thr Val Thr Ser Lys Asn Asn Asp
    130                 135                 140

Asp Glu Gln Tyr Val Trp Glu Ser Ser Ala Gly Gly Ser Phe Thr Val
145                 150                 155                 160

Arg Ala Asp Asn Ser Glu Pro Leu Gly Arg Gly Thr Lys Ile Val Leu
                165                 170                 175

Tyr Ile Lys Glu Asp Gln Thr Asp Tyr Leu Glu Glu Ser Lys Ile Lys
            180                 185                 190

Glu Ile Val Asn Lys His Ser Gln Phe Ile Gly Tyr Pro Ile Lys Leu
        195                 200                 205

Leu Val Glu Lys Glu Arg Glu Lys Glu Val Ser Asp Asp Glu Ala Asp
    210                 215                 220
```

-continued

```
Asp Glu Lys Lys Glu Gly Asp Glu Lys Glu Met Glu Thr Asp Glu
225                 230                 235                 240

Pro Lys Ile Glu Asp Val Gly Glu Asp Glu Asp Ala Asp Lys Lys Asp
            245                 250                 255

Lys Asp Ala Lys Lys Lys Thr Ile Lys Glu Lys Tyr Thr Glu Asp
            260                 265                 270

Glu Glu Leu Asn Lys Thr Lys Pro Ile Trp Thr Arg Asn Pro Asp Asp
        275                 280                 285

Ile Ser Gln Glu Glu Tyr Gly Glu Phe Tyr Lys Ser Leu Thr Asn Asp
        290                 295                 300

Trp Glu Asp His Leu Ala Val Lys His Phe Ser Val Glu Gly Gln Leu
305                 310                 315                 320

Glu Phe Arg Ala Leu Phe Ile Pro Arg Arg Thr Pro Phe Asp Leu
            325                 330                 335

Phe Glu Asn Gln Lys Lys Arg Asn Asn Ile Lys Leu Tyr Val Arg Arg
            340                 345                 350

Val Phe Ile Met Asp Asn Cys Glu Asp Leu Ile Pro Glu Tyr Leu Asn
            355                 360                 365

Phe Met Lys Gly Val Val Asp Ser Glu Asp Leu Pro Leu Asn Ile Ser
    370                 375                 380

Arg Glu Met Leu Gln Gln Asn Lys Val Leu Lys Val Ile Arg Lys Asn
385                 390                 395                 400

Leu Val Lys Lys Thr Met Glu Leu Ile Glu Glu Leu Thr Glu Asp Lys
            405                 410                 415

Glu Asn Tyr Lys Lys Phe Tyr Asp Gln Phe Ser Lys Asn Leu Lys Leu
            420                 425                 430

Gly Val His Glu Asp Ser Asn Asn Arg Ala Lys Leu Ala Asp Phe Leu
        435                 440                 445

Arg Phe His Thr Ser Ala Ser Gly Asp Asp Phe Cys Ser Leu Ala Asp
    450                 455                 460

Tyr Val Ser Arg Met Lys Asp Asn Gln Lys His Val Tyr Phe Ile Thr
465                 470                 475                 480

Gly Glu Ser Lys Asp Gln Val Ser Asn Ser Ala Phe Val Glu Arg Val
            485                 490                 495

Lys Ala Arg Gly Phe Glu Val Val Tyr Met Thr Glu Pro Ile Asp Glu
            500                 505                 510

Tyr Val Ile Gln His Leu Lys Glu Tyr Lys Gly Lys Gln Leu Val Ser
        515                 520                 525

Val Thr Lys Glu Gly Leu Glu Leu Pro Glu Asp Glu Ser Glu Lys Lys
    530                 535                 540

Lys Arg Glu Glu Asp Lys Ala Lys Phe Glu Ser Leu Cys Lys Leu Met
545                 550                 555                 560

Lys Ser Ile Leu Asp Asn Lys Val Glu Lys Val Val Ser Asn Arg
            565                 570                 575

Leu Val Asp Ser Pro Cys Cys Ile Val Thr Ser Gln Phe Gly Trp Ser
            580                 585                 590

Ala Asn Met Glu Arg Ile Met Lys Ala Gln Ala Leu Arg Asp Thr Ala
    595                 600                 605

Thr Met Gly Tyr Met Ala Gly Lys Lys Gln Leu Glu Ile Asn Pro Asp
        610                 615                 620

His Pro Ile Val Glu Thr Leu Arg Gln Lys Ala Asp Ala Asp Lys Asn
625                 630                 635                 640

Asp Lys Ala Val Lys Asp Leu Val Ile Leu Leu Phe Glu Thr Ser Leu
```

|     |     |     |     |     |     |     |     |     |     |     |
| --- | --- | --- | --- | --- | --- | --- | --- | --- | --- | --- |
|     |     | 645 |     |     |     | 650 |     |     |     | 655 |
| Leu | Ser | Ser | Gly | Phe | Ser | Leu | Asp | Ser | Pro | Gln | Val | His | Ala | Ser | Arg |
|     |     |     |     | 660 |     |     |     |     | 665 |     |     |     |     | 670 |     |

Ile Tyr Arg Met Ile Lys Leu Gly Leu Gly Ile Asp Glu Asp Glu Pro
            675             680             685

Met Thr Thr Asp Asp Ala Gln Ser Ala Gly Asp Ala Pro Ser Leu Val
      690             695             700

Glu Asp Thr Glu Asp Ala Ser His Met Glu Glu Val Asp
705             710             715

<210> SEQ ID NO 3
<211> LENGTH: 2912
<212> TYPE: DNA
<213> ORGANISM: Homo sapiens
<220> FEATURE:
<221> NAME/KEY: CDS
<222> LOCATION: (61)..(2256)

<400> SEQUENCE: 3
cagttgcttc agcgtcccgg tgtggctgtg ccgttggtcc tgtgcggtca cttagccaag    60 atg cct gag gaa acc cag acc caa gac caa ccg atg gag gag gag gag   108
Met Pro Glu Glu Thr Gln Thr Gln Asp Gln Pro Met Glu Glu Glu Glu
 1               5                  10                  15 gtt gag acg ttc gcc ttt cag gca gaa att gcc cag ttg atg tca ttg   156
Val Glu Thr Phe Ala Phe Gln Ala Glu Ile Ala Gln Leu Met Ser Leu
                20                  25                  30 atc atc aat act ttc tac tcg aac aaa gag atc ttt ctg aga gag ctc   204
Ile Ile Asn Thr Phe Tyr Ser Asn Lys Glu Ile Phe Leu Arg Glu Leu
            35                  40                  45 att tca aat tca tca gat gca ttg gac aaa atc cgg tat gaa act ttg   252
Ile Ser Asn Ser Ser Asp Ala Leu Asp Lys Ile Arg Tyr Glu Thr Leu
        50                  55                  60 aca gat ccc agt aaa tta gac tct ggg aaa gag ctg cat att aac ctt   300
Thr Asp Pro Ser Lys Leu Asp Ser Gly Lys Glu Leu His Ile Asn Leu
 65                  70                  75                  80 ata ccg aac aaa caa gat cga act ctc act att gtg gat act gga att   348
Ile Pro Asn Lys Gln Asp Arg Thr Leu Thr Ile Val Asp Thr Gly Ile
                 85                  90                  95 gga atg acc aag gct gac ttg atc aat aac ctt ggt act atc gcc aag   396
Gly Met Thr Lys Ala Asp Leu Ile Asn Asn Leu Gly Thr Ile Ala Lys
            100                 105                 110 tct ggg acc aaa gcg ttc atg gaa gct ttg cag gct ggt gca gat atc   444
Ser Gly Thr Lys Ala Phe Met Glu Ala Leu Gln Ala Gly Ala Asp Ile
        115                 120                 125 tct atg att ggc cag ttc ggt gtt ggt ttt tat tct gct tat ttg gtt   492
Ser Met Ile Gly Gln Phe Gly Val Gly Phe Tyr Ser Ala Tyr Leu Val
130                 135                 140 gct gag aaa gta act gtg atc acc aaa cat aac gat gat gag cag tac   540
Ala Glu Lys Val Thr Val Ile Thr Lys His Asn Asp Asp Glu Gln Tyr
145                 150                 155                 160 gct tgg gag tcc tca gca ggg gga tca ttc aca gtg agg aca gac aca   588
Ala Trp Glu Ser Ser Ala Gly Gly Ser Phe Thr Val Arg Thr Asp Thr
                165                 170                 175 ggt gaa cct atg ggt cgt gga aca aaa gtt atc cta cac ctg aaa gaa   636
Gly Glu Pro Met Gly Arg Gly Thr Lys Val Ile Leu His Leu Lys Glu
            180                 185                 190 gac caa act gag tac ttg gag gaa cga aga ata aag gag att gtg aag   684
Asp Gln Thr Glu Tyr Leu Glu Glu Arg Arg Ile Lys Glu Ile Val Lys
        195                 200                 205

| | | |
|---|---|---|
| aaa cat tct cag ttt att gga tat ccc att act ctt ttt gtg gag aag<br>Lys His Ser Gln Phe Ile Gly Tyr Pro Ile Thr Leu Phe Val Glu Lys<br>210                      215                    220 | 732 |
| gaa cgt gat aaa gaa gta agc gat gat gag gct gaa gaa aag gaa gac<br>Glu Arg Asp Lys Glu Val Ser Asp Asp Glu Ala Glu Glu Lys Glu Asp<br>225                      230                    235                    240 | 780 |
| aaa gaa gaa gaa aaa gaa aaa gaa gag aaa gag tcg gaa gac aaa cct<br>Lys Glu Glu Glu Lys Glu Lys Glu Glu Lys Glu Ser Glu Asp Lys Pro<br>                  245                    250                    255 | 828 |
| gaa att gaa gat gtt ggt tct gat gag gaa gaa gaa aag aag gat ggt<br>Glu Ile Glu Asp Val Gly Ser Asp Glu Glu Glu Glu Lys Lys Asp Gly<br>         260                    265                    270 | 876 |
| gac aag aag aag aag aag aag att aag gaa aag tac atc gat caa gaa<br>Asp Lys Lys Lys Lys Lys Lys Ile Lys Glu Lys Tyr Ile Asp Gln Glu<br>275                      280                    285 | 924 |
| gag ctc aac aaa aca aag ccc atc tgg acc aga aat ccc gac gat att<br>Glu Leu Asn Lys Thr Lys Pro Ile Trp Thr Arg Asn Pro Asp Asp Ile<br>         290                    295                    300 | 972 |
| act aat gag gag tac gga gaa ttc tat aag agc ttg acc aat gac tgg<br>Thr Asn Glu Glu Tyr Gly Glu Phe Tyr Lys Ser Leu Thr Asn Asp Trp<br>305                      310                    315                    320 | 1020 |
| gaa gat cac ttg gca gtg aag cat ttt tca gtt gaa gga cag ttg gaa<br>Glu Asp His Leu Ala Val Lys His Phe Ser Val Glu Gly Gln Leu Glu<br>                        325                    330                    335 | 1068 |
| ttc aga gcc ctt cta ttt gtc cca cga cgt gct cct ttt gat ctg ttt<br>Phe Arg Ala Leu Leu Phe Val Pro Arg Arg Ala Pro Phe Asp Leu Phe<br>         340                    345                    350 | 1116 |
| gaa aac aga aag aaa aag aac aat atc aaa ttg tat gta cgc aga gtt<br>Glu Asn Arg Lys Lys Lys Asn Asn Ile Lys Leu Tyr Val Arg Arg Val<br>355                      360                    365 | 1164 |
| ttc atc atg gat aac tgt gag gag cta atc cct gaa tat ctg aac ttc<br>Phe Ile Met Asp Asn Cys Glu Glu Leu Ile Pro Glu Tyr Leu Asn Phe<br>         370                    375                    380 | 1212 |
| att aga ggg gtg gta gac tcg gag gat ctc cct cta aac ata tcc cgt<br>Ile Arg Gly Val Val Asp Ser Glu Asp Leu Pro Leu Asn Ile Ser Arg<br>385                      390                    395                    400 | 1260 |
| gag atg ttg caa caa agc aaa att ttg aaa gtt atc agg aag aat ttg<br>Glu Met Leu Gln Gln Ser Lys Ile Leu Lys Val Ile Arg Lys Asn Leu<br>                        405                    410                    415 | 1308 |
| gtc aaa aaa tgc tta gaa ctc ttt act gaa ctg gcg gaa gat aaa gag<br>Val Lys Lys Cys Leu Glu Leu Phe Thr Glu Leu Ala Glu Asp Lys Glu<br>         420                    425                    430 | 1356 |
| aac tac aag aaa ttc tat gag cag ttc tct aaa aac ata aag ctt gga<br>Asn Tyr Lys Lys Phe Tyr Glu Gln Phe Ser Lys Asn Ile Lys Leu Gly<br>435                      440                    445 | 1404 |
| ata cac gaa gac tct caa aat cgg aag aag ctt tca gag ctg tta agg<br>Ile His Glu Asp Ser Gln Asn Arg Lys Lys Leu Ser Glu Leu Leu Arg<br>450                      455                    460 | 1452 |
| tac tac aca tct gcc tct ggt gat gag atg gtt tct ctc aag gac tac<br>Tyr Tyr Thr Ser Ala Ser Gly Asp Glu Met Val Ser Leu Lys Asp Tyr<br>465                      470                    475                    480 | 1500 |
| tgc acc aga atg aag gag aac cag aaa cat atc tat tat atc aca ggt<br>Cys Thr Arg Met Lys Glu Asn Gln Lys His Ile Tyr Tyr Ile Thr Gly<br>                        485                    490                    495 | 1548 |
| gag acc aag gac cag gta gct aac tca gcc ttt gtg gaa cgt ctt cgg<br>Glu Thr Lys Asp Gln Val Ala Asn Ser Ala Phe Val Glu Arg Leu Arg<br>         500                    505                    510 | 1596 |
| aaa cat ggc tta gaa gtg atc tat atg att gag ccc att gat gag tac<br>Lys His Gly Leu Glu Val Ile Tyr Met Ile Glu Pro Ile Asp Glu Tyr<br>515                      520                    525 | 1644 |

```
tgt gtc caa cag ctg aag gaa ttt gag ggg aag act tta gtg tca gtc    1692
Cys Val Gln Gln Leu Lys Glu Phe Glu Gly Lys Thr Leu Val Ser Val
530             535                 540 acc aaa gaa ggc ctg gaa ctt cca gag gat gaa gaa gag aaa aag aag    1740
Thr Lys Glu Gly Leu Glu Leu Pro Glu Asp Glu Glu Glu Lys Lys Lys
545             550                 555                 560 cag gaa gag aaa aaa aca aag ttt gag aac ctc tgc aaa atc atg aaa    1788
Gln Glu Glu Lys Lys Thr Lys Phe Glu Asn Leu Cys Lys Ile Met Lys
                565                 570                 575 gac ata ttg gag aaa aaa gtt gaa aag gtg gtt gtg tca aac cga ttg    1836
Asp Ile Leu Glu Lys Lys Val Glu Lys Val Val Val Ser Asn Arg Leu
            580                 585                 590 gtg aca tct cca tgc tgt att gtc aca agc aca tat ggc tgg aca gca    1884
Val Thr Ser Pro Cys Cys Ile Val Thr Ser Thr Tyr Gly Trp Thr Ala
        595                 600                 605 aac atg gag aga atc atg aaa gct caa gcc cta aga gac aac tca aca    1932
Asn Met Glu Arg Ile Met Lys Ala Gln Ala Leu Arg Asp Asn Ser Thr
    610                 615                 620 atg ggt tac atg gca gca aag aaa cac ctg gag ata aac cct gac cat    1980
Met Gly Tyr Met Ala Ala Lys Lys His Leu Glu Ile Asn Pro Asp His
625                 630                 635                 640 tcc att att gag acc tta agg caa aag gca gag gct gat aag aac gac    2028
Ser Ile Ile Glu Thr Leu Arg Gln Lys Ala Glu Ala Asp Lys Asn Asp
                645                 650                 655 aag tct gtg aag gat ctg gtc atc ttg ctt tat gaa act gcg ctc ctg    2076
Lys Ser Val Lys Asp Leu Val Ile Leu Leu Tyr Glu Thr Ala Leu Leu
            660                 665                 670 tct tct ggc ttc agt ctg gaa gat ccc cag aca cat gct aac agg atc    2124
Ser Ser Gly Phe Ser Leu Glu Asp Pro Gln Thr His Ala Asn Arg Ile
        675                 680                 685 tac agg atg atc aaa ctt ggt ctg ggt att gat gaa gat gac cct act    2172
Tyr Arg Met Ile Lys Leu Gly Leu Gly Ile Asp Glu Asp Asp Pro Thr
    690                 695                 700 gct gat gat acc agt gct gct gta act gaa gaa atg cca ccc ctt gaa    2220
Ala Asp Asp Thr Ser Ala Ala Val Thr Glu Glu Met Pro Pro Leu Glu
705                 710                 715                 720 gga gat gac gac aca tca cgc atg gaa gaa gta gac taatctctgg         2266
Gly Asp Asp Asp Thr Ser Arg Met Glu Glu Val Asp
                725                 730 ctgagggatg acttacctgt tcagtactct acaattcctc tgataatata ttttcaagga  2326 tgttttctt tattttgtt aatattaaaa agtctgtatg gcatgacaac tactttaagg    2386
ggaagataag atttctgtct actaagtgat gctgtgatac cttaggcact aaagcagagc  2446
tagtaatgct ttttgagttt catgttggtt ctttcacaga tggggtaacg tgcactgtaa  2506
gacgtatgta acatgatgtt aactttgtgt ggtctaaagt gtttagctgt caagccggat  2566
gcctaagtag accaaatctt gttattgaag tgttctgagc tgtatcttga tgtttagaaa  2626
agtattcgtt acatcttgta ggatctactt tttgaacttt tcattccctg tagttgacaa  2686
ttctgcatgt actagtcctc tagaaatagg ttaaactgaa gcaacttgat ggaaggatct  2746
ctccacaggg cttgttttcc aaagaaaagt attgtttgga ggagcaaagt taaaagccta  2806
cctaagcata tcgtaaagct gttcaaatac tcgagcccag tcttgtggat ggaaatgtag  2866
tgctcgagtc acattctgct taagttgta acaaatacag atgagt                 2912

<210> SEQ ID NO 4
<211> LENGTH: 732
<212> TYPE: PRT
```

<213> ORGANISM: Homo sapiens

<400> SEQUENCE: 4

```
Met Pro Glu Glu Thr Gln Thr Gln Asp Gln Pro Met Glu Glu Glu
 1               5                  10                  15

Val Glu Thr Phe Ala Phe Gln Ala Glu Ile Ala Gln Leu Met Ser Leu
                20                  25                  30

Ile Ile Asn Thr Phe Tyr Ser Asn Lys Glu Ile Phe Leu Arg Glu Leu
                35                  40                  45

Ile Ser Asn Ser Ser Asp Ala Leu Asp Lys Ile Arg Tyr Glu Thr Leu
 50                  55                  60

Thr Asp Pro Ser Lys Leu Asp Ser Gly Lys Glu Leu His Ile Asn Leu
 65                  70                  75                  80

Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
                100                 105                 110

Ser Gly Thr Lys Ala Phe Met Glu Ala Leu Gln Ala Gly Ala Asp Ile
                115                 120                 125

Ser Met Ile Gly Gln Phe Gly Val Gly Phe Tyr Ser Ala Tyr Leu Val
130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
                180                 185                 190

Asp Gln Thr Glu Tyr Leu Glu Glu Arg Arg Ile Lys Glu Ile Val Lys
                195                 200                 205

Lys His Ser Gln Phe Ile Gly Tyr Pro Ile Thr Leu Phe Val Glu Lys
        210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Glu Lys Lys Asp Gly
                260                 265                 270

Asp Lys Lys Lys Lys Lys Ile Lys Glu Lys Tyr Ile Asp Gln Glu
        275                 280                 285

Glu Leu Asn Lys Thr Lys Pro Ile Trp Thr Arg Asn Pro Asp Asp Ile
        290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
                325                 330                 335

Phe Arg Ala Leu Leu Phe Val Pro Arg Arg Ala Pro Phe Asp Leu Phe
                340                 345                 350

Glu Asn Arg Lys Lys Lys Asn Asn Ile Lys Leu Tyr Val Arg Arg Val
                355                 360                 365

Phe Ile Met Asp Asn Cys Glu Glu Leu Ile Pro Glu Tyr Leu Asn Phe
                370                 375                 380

Ile Arg Gly Val Val Asp Ser Glu Asp Leu Pro Leu Asn Ile Ser Arg
385                 390                 395                 400
```

-continued

Glu Met Leu Gln Gln Ser Lys Ile Leu Lys Val Ile Arg Lys Asn Leu
            405                 410                 415

Val Lys Lys Cys Leu Glu Leu Phe Thr Glu Leu Ala Glu Asp Lys Glu
            420                 425                 430

Asn Tyr Lys Lys Phe Tyr Glu Gln Phe Ser Lys Asn Ile Lys Leu Gly
            435                 440                 445

Ile His Glu Asp Ser Gln Asn Arg Lys Lys Leu Ser Glu Leu Leu Arg
            450                 455                 460

Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
            485                 490                 495

Glu Thr Lys Asp Gln Val Ala Asn Ser Ala Phe Val Glu Arg Leu Arg
            500                 505                 510

Lys His Gly Leu Glu Val Ile Tyr Met Ile Glu Pro Ile Asp Glu Tyr
            515                 520                 525

Cys Val Gln Gln Leu Lys Glu Phe Glu Gly Lys Thr Leu Val Ser Val
            530                 535                 540

Thr Lys Glu Gly Leu Glu Leu Pro Glu Asp Glu Glu Glu Lys Lys Lys
545                 550                 555                 560

Gln Glu Glu Lys Lys Thr Lys Phe Glu Asn Leu Cys Lys Ile Met Lys
            565                 570                 575

Asp Ile Leu Glu Lys Lys Val Glu Lys Val Val Val Ser Asn Arg Leu
            580                 585                 590

Val Thr Ser Pro Cys Cys Ile Val Thr Ser Thr Tyr Gly Trp Thr Ala
            595                 600                 605

Asn Met Glu Arg Ile Met Lys Ala Gln Ala Leu Arg Asp Asn Ser Thr
            610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
            645                 650                 655

Lys Ser Val Lys Asp Leu Val Ile Leu Leu Tyr Glu Thr Ala Leu Leu
            660                 665                 670

Ser Ser Gly Phe Ser Leu Glu Asp Pro Gln Thr His Ala Asn Arg Ile
            675                 680                 685

Tyr Arg Met Ile Lys Leu Gly Leu Gly Ile Asp Glu Asp Pro Thr
            690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
            725                 730

<210> SEQ ID NO 5
<211> LENGTH: 2543
<212> TYPE: DNA
<213> ORGANISM: Homo sapiens
<220> FEATURE:
<221> NAME/KEY: CDS
<222> LOCATION: (85)..(2256)

<400> SEQUENCE: 5
ctccggcgca gtgttgggac tgtctgggta tcggaaagca agcctacgtt gctcactatt      60
acgtataatc cttttctttt caag atg cct gag gaa gtg cac cat gga gag        111
                          Met Pro Glu Glu Val His His Gly Glu
                          1               5

```
gag gag gtg gag act ttt gcc ttt cag gca gaa att gcc caa ctc atg    159
Glu Glu Val Glu Thr Phe Ala Phe Gln Ala Glu Ile Ala Gln Leu Met
 10              15                  20                  25 tcc ctc atc atc aat acc ttc tat tcc aac aag gag att ttc ctt cgg    207
Ser Leu Ile Ile Asn Thr Phe Tyr Ser Asn Lys Glu Ile Phe Leu Arg
             30                  35                  40 gag ttg atc tct aat gct tct gat gcc ttg gac aag att cgc tat gag    255
Glu Leu Ile Ser Asn Ala Ser Asp Ala Leu Asp Lys Ile Arg Tyr Glu
             45                  50                  55 agc ctg aca gac cct tcg aag ttg gac agt ggt aaa gag ctg aaa att    303
Ser Leu Thr Asp Pro Ser Lys Leu Asp Ser Gly Lys Glu Leu Lys Ile
         60                  65                  70 gac atc atc ccc aac cct cag gaa cgt acc ctg act ttg gta gac aca    351
Asp Ile Ile Pro Asn Pro Gln Glu Arg Thr Leu Thr Leu Val Asp Thr
 75                  80                  85 ggc att ggc atg acc aaa gct gat ctc ata aat aat ttg gga acc att    399
Gly Ile Gly Met Thr Lys Ala Asp Leu Ile Asn Asn Leu Gly Thr Ile
 90                  95                 100                 105 gcc aag tct ggt act aaa gca ttc atg gag gct ctt cag gct ggt gca    447
Ala Lys Ser Gly Thr Lys Ala Phe Met Glu Ala Leu Gln Ala Gly Ala
             110                 115                 120 gac atc tcc atg att ggg cag ttt ggt gtt ggc ttt tat tct gcc tac    495
Asp Ile Ser Met Ile Gly Gln Phe Gly Val Gly Phe Tyr Ser Ala Tyr
             125                 130                 135 ttg gtg gca gag aaa gtg gtt gtg atc aga aag cac aac gat gat gaa    543
Leu Val Ala Glu Lys Val Val Val Ile Arg Lys His Asn Asp Asp Glu
             140                 145                 150 cag tat gct tgg gag tct tct gct gga ggt tcc ttc act gtg cgt gct    591
Gln Tyr Ala Trp Glu Ser Ser Ala Gly Gly Ser Phe Thr Val Arg Ala
 155                 160                 165 gac cat ggt gag ccc att ggc atg ggt acc aaa gtg atc ctc cat ctt    639
Asp His Gly Glu Pro Ile Gly Met Gly Thr Lys Val Ile Leu His Leu
170                 175                 180                 185 aaa gaa gat cag aca gag tac cta gaa gag agg cgg gtc aaa gaa gta    687
Lys Glu Asp Gln Thr Glu Tyr Leu Glu Glu Arg Arg Val Lys Glu Val
             190                 195                 200 gtg aag aag cat tct cag ttc ata ggc tat ccc atc acc ctt tat ttg    735
Val Lys Lys His Ser Gln Phe Ile Gly Tyr Pro Ile Thr Leu Tyr Leu
             205                 210                 215 gag aag gaa cga gag aag gaa att agt gat gat gag gca gag gaa gag    783
Glu Lys Glu Arg Glu Lys Glu Ile Ser Asp Asp Glu Ala Glu Glu Glu
             220                 225                 230 aaa ggt gag aaa gaa gag gaa gat aaa gat gat gaa gaa aag ccc aag    831
Lys Gly Glu Lys Glu Glu Glu Asp Lys Asp Asp Glu Glu Lys Pro Lys
             235                 240                 245 atc gaa gat gtg ggt tca gat gag gag gat gac agc ggt aag gat aag    879
Ile Glu Asp Val Gly Ser Asp Glu Glu Asp Asp Ser Gly Lys Asp Lys
250                 255                 260                 265 aag aag aaa act aag aag atc aaa gag aaa tac att gat cag gaa gaa    927
Lys Lys Lys Thr Lys Lys Ile Lys Glu Lys Tyr Ile Asp Gln Glu Glu
             270                 275                 280 cta aac aag acc aag cct att tgg acc aga aac cct gat gac atc acc    975
Leu Asn Lys Thr Lys Pro Ile Trp Thr Arg Asn Pro Asp Asp Ile Thr
             285                 290                 295 caa gag gag tat gga gaa ttc tac aag agc ctc act aat gac tgg gaa   1023
Gln Glu Glu Tyr Gly Glu Phe Tyr Lys Ser Leu Thr Asn Asp Trp Glu
             300                 305                 310 gac cac ttg gca gtc aag cac ttt tct gta gaa ggt cag ttg gaa ttc   1071
Asp His Leu Ala Val Lys His Phe Ser Val Glu Gly Gln Leu Glu Phe
```

-continued

```
            315                 320                 325
agg gca ttg cta ttt att cct cgt cgg gct ccc ttt gac ctt ttt gag    1119
Arg Ala Leu Leu Phe Ile Pro Arg Arg Ala Pro Phe Asp Leu Phe Glu
330                 335                 340                 345 aac aag aag aaa aag aac aac atc aaa ctc tat gtc cgc cgt gtg ttc    1167
Asn Lys Lys Lys Lys Asn Asn Ile Lys Leu Tyr Val Arg Arg Val Phe
                350                 355                 360 atc atg gac agc tgt gat gag ttg ata cca gag tat ctc aat ttt atc    1215
Ile Met Asp Ser Cys Asp Glu Leu Ile Pro Glu Tyr Leu Asn Phe Ile
                365                 370                 375 cgt ggt gtg gtt gac tct gag gat ctg ccc ctg aac atc tcc cga gaa    1263
Arg Gly Val Val Asp Ser Glu Asp Leu Pro Leu Asn Ile Ser Arg Glu
                380                 385                 390 atg ctc cag cag agc aaa atc ttg aaa gtc att cgc aaa aac att gtt    1311
Met Leu Gln Gln Ser Lys Ile Leu Lys Val Ile Arg Lys Asn Ile Val
395                 400                 405 aag aag tgc ctt gag ctc ttc tct gag ctg gca gaa gac aag gag aat    1359
Lys Lys Cys Leu Glu Leu Phe Ser Glu Leu Ala Glu Asp Lys Glu Asn
410                 415                 420                 425 tac aag aaa ttc tat gag gca ttc tct aaa aat ctc aag ctt gga atc    1407
Tyr Lys Lys Phe Tyr Glu Ala Phe Ser Lys Asn Leu Lys Leu Gly Ile
                430                 435                 440 cac gaa gac tcc act aac cgc cgc cgc ctg tct gag ctg ctg cgc tat    1455
His Glu Asp Ser Thr Asn Arg Arg Arg Leu Ser Glu Leu Leu Arg Tyr
                445                 450                 455 cat acc tcc cag tct gga gat gag atg aca tct ctg tca gag tat gtt    1503
His Thr Ser Gln Ser Gly Asp Glu Met Thr Ser Leu Ser Glu Tyr Val
                460                 465                 470 tct cgc atg aag gag aca cag aag tcc atc tat tac atc act ggt gag    1551
Ser Arg Met Lys Glu Thr Gln Lys Ser Ile Tyr Tyr Ile Thr Gly Glu
475                 480                 485 agc aaa gag cag gtg gcc aac tca gct ttt gtg gag cga gtg cgg aaa    1599
Ser Lys Glu Gln Val Ala Asn Ser Ala Phe Val Glu Arg Val Arg Lys
490                 495                 500                 505 cgg ggc ttc gag gtg gta tat atg acc gag ccc att gac gag tac tgt    1647
Arg Gly Phe Glu Val Val Tyr Met Thr Glu Pro Ile Asp Glu Tyr Cys
                510                 515                 520 gtg cag cag ctc aag gaa ttt gat ggg aag agc ctg gtc tca gtt acc    1695
Val Gln Gln Leu Lys Glu Phe Asp Gly Lys Ser Leu Val Ser Val Thr
                525                 530                 535 aag gag ggt ctg gag ctg cct gag gat gag gag gag aag aag aag atg    1743
Lys Glu Gly Leu Glu Leu Pro Glu Asp Glu Glu Glu Lys Lys Lys Met
                540                 545                 550 gaa gag agc aag gca aag ttt gag aac ctc tgc aag ctc atg aaa gaa    1791
Glu Glu Ser Lys Ala Lys Phe Glu Asn Leu Cys Lys Leu Met Lys Glu
555                 560                 565 atc tta gat aag aag gtt gag aag gtg aca atc tcc aat aga ctt gtg    1839
Ile Leu Asp Lys Lys Val Glu Lys Val Thr Ile Ser Asn Arg Leu Val
570                 575                 580                 585 tct tca cct tgc tgc att gtg acc agc acc tac ggc tgg aca gcc aat    1887
Ser Ser Pro Cys Cys Ile Val Thr Ser Thr Tyr Gly Trp Thr Ala Asn
                590                 595                 600 atg gag cgg atc atg aaa gcc cag gca ctt cgg gac aac tcc acc atg    1935
Met Glu Arg Ile Met Lys Ala Gln Ala Leu Arg Asp Asn Ser Thr Met
                605                 610                 615 ggc tat atg atg gcc aaa aag cac ctg gag atc aac cct gac cac ccc    1983
Gly Tyr Met Met Ala Lys Lys His Leu Glu Ile Asn Pro Asp His Pro
                620                 625                 630 att gtg gag acg ctg cgg cag aag gct gag gcc gac aag aat gat aag    2031
```

-continued

```
Ile Val Glu Thr Leu Arg Gln Lys Ala Glu Ala Asp Lys Asn Asp Lys
    635                 640                 645 gca gtt aag gac ctg gtg gtg ctg ctg ttt gaa acc gcc ctg cta tct      2079
Ala Val Lys Asp Leu Val Val Leu Leu Phe Glu Thr Ala Leu Leu Ser
650                 655                 660                 665 tct ggc ttt tcc ctt gag gat ccc cag acc cac tcc aac cgc atc tat      2127
Ser Gly Phe Ser Leu Glu Asp Pro Gln Thr His Ser Asn Arg Ile Tyr
                670                 675                 680 cgc atg atc aag cta ggt cta ggt att gat gaa gat gaa gtg gca gca      2175
Arg Met Ile Lys Leu Gly Leu Gly Ile Asp Glu Asp Glu Val Ala Ala
            685                 690                 695 gag gaa ccc aat gct gca gtt cct gat gag atc ccc cct ctc gag ggc      2223
Glu Glu Pro Asn Ala Ala Val Pro Asp Glu Ile Pro Pro Leu Glu Gly
        700                 705                 710 gat gag gat gcg tct cgc atg gaa gaa gtc gat taggttagga gttcatagtt    2276
Asp Glu Asp Ala Ser Arg Met Glu Glu Val Asp
    715                 720 ggaaaacttg tgcccttgta tagtgtcccc atgggctccc actgcagcct cgagtgcccc    2336
tgtcccacct ggctccccct gctggtgtct agtgtttttt ccctctcct gtccttgtgt     2396 tgaaggcagt aaactaaggg tgtcaagccc cattccctct ctactcttga cagcaggatt    2456
ggatgttgtg tattgtggtt tatttattt tcttcatttt gttctgaaat taaagtatgc     2516
aaaataaaga atatgccgtt tttatac                                         2543
```

<210> SEQ ID NO 6
<211> LENGTH: 724
<212> TYPE: PRT
<213> ORGANISM: Homo sapiens

<400> SEQUENCE: 6

```
Met Pro Glu Glu Val His His Gly Glu Glu Val Glu Thr Phe Ala
  1               5                  10                  15

Phe Gln Ala Glu Ile Ala Gln Leu Met Ser Leu Ile Ile Asn Thr Phe
                20                  25                  30

Tyr Ser Asn Lys Glu Ile Phe Leu Arg Glu Leu Ile Ser Asn Ala Ser
            35                  40                  45

Asp Ala Leu Asp Lys Ile Arg Tyr Glu Ser Leu Thr Asp Pro Ser Lys
        50                  55                  60

Leu Asp Ser Gly Lys Glu Leu Lys Ile Asp Ile Ile Pro Asn Pro Gln
    65                  70                  75                  80

Glu Arg Thr Leu Thr Leu Val Asp Thr Gly Ile Gly Met Thr Lys Ala
                85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
        115                 120                 125

Phe Gly Val Gly Phe Tyr Ser Ala Tyr Leu Val Ala Glu Lys Val Val
    130                 135                 140

Val Ile Arg Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Met Gly Thr Lys Val Ile Leu His Leu Lys Glu Asp Gln Thr Glu Tyr
            180                 185                 190

Leu Glu Glu Arg Arg Val Lys Glu Val Val Lys Lys His Ser Gln Phe
        195                 200                 205
```

-continued

```
Ile Gly Tyr Pro Ile Thr Leu Tyr Leu Glu Lys Glu Arg Glu Lys Glu
    210                 215                 220
Ile Ser Asp Asp Glu Ala Glu Glu Lys Gly Glu Lys Glu Glu Glu
225                 230                 235                 240
Asp Lys Asp Asp Glu Glu Lys Pro Lys Ile Glu Asp Val Gly Ser Asp
                245                 250                 255
Glu Glu Asp Asp Ser Gly Lys Asp Lys Lys Lys Thr Lys Lys Ile
                260                 265                 270
Lys Glu Lys Tyr Ile Asp Gln Glu Leu Asn Lys Thr Lys Pro Ile
                275                 280                 285
Trp Thr Arg Asn Pro Asp Asp Ile Thr Gln Glu Glu Tyr Gly Glu Phe
    290                 295                 300
Tyr Lys Ser Leu Thr Asn Asp Trp Glu Asp His Leu Ala Val Lys His
305                 310                 315                 320
Phe Ser Val Glu Gly Gln Leu Glu Phe Arg Ala Leu Leu Phe Ile Pro
                325                 330                 335
Arg Arg Ala Pro Phe Asp Leu Phe Glu Asn Lys Lys Lys Asn Asn
                340                 345                 350
Ile Lys Leu Tyr Val Arg Arg Val Phe Ile Met Asp Ser Cys Asp Glu
                355                 360                 365
Leu Ile Pro Glu Tyr Leu Asn Phe Ile Arg Gly Val Val Asp Ser Glu
    370                 375                 380
Asp Leu Pro Leu Asn Ile Ser Arg Glu Met Leu Gln Gln Ser Lys Ile
385                 390                 395                 400
Leu Lys Val Ile Arg Lys Asn Ile Val Lys Lys Cys Leu Glu Leu Phe
                405                 410                 415
Ser Glu Leu Ala Glu Asp Lys Glu Asn Tyr Lys Lys Phe Tyr Glu Ala
                420                 425                 430
Phe Ser Lys Asn Leu Lys Leu Gly Ile His Glu Asp Ser Thr Asn Arg
    435                 440                 445
Arg Arg Leu Ser Glu Leu Leu Arg Tyr His Thr Ser Gln Ser Gly Asp
    450                 455                 460
Glu Met Thr Ser Leu Ser Glu Tyr Val Ser Arg Met Lys Glu Thr Gln
465                 470                 475                 480
Lys Ser Ile Tyr Tyr Ile Thr Gly Glu Ser Lys Glu Gln Val Ala Asn
                485                 490                 495
Ser Ala Phe Val Glu Arg Val Arg Lys Arg Gly Phe Glu Val Val Tyr
                500                 505                 510
Met Thr Glu Pro Ile Asp Glu Tyr Cys Val Gln Gln Leu Lys Glu Phe
    515                 520                 525
Asp Gly Lys Ser Leu Val Ser Val Thr Lys Glu Gly Leu Glu Leu Pro
    530                 535                 540
Glu Asp Glu Glu Glu Lys Lys Lys Met Glu Glu Ser Lys Ala Lys Phe
545                 550                 555                 560
Glu Asn Leu Cys Lys Leu Met Lys Glu Ile Leu Asp Lys Lys Val Glu
                565                 570                 575
Lys Val Thr Ile Ser Asn Arg Leu Val Ser Ser Pro Cys Cys Ile Val
                580                 585                 590
Thr Ser Thr Tyr Gly Trp Thr Ala Asn Met Glu Arg Ile Met Lys Ala
                595                 600                 605
Gln Ala Leu Arg Asp Asn Ser Thr Met Gly Tyr Met Met Ala Lys Lys
    610                 615                 620
```

-continued

```
His Leu Glu Ile Asn Pro Asp His Pro Ile Val Glu Thr Leu Arg Gln
625                 630                 635                 640

Lys Ala Glu Ala Asp Lys Asn Asp Lys Ala Val Lys Asp Leu Val Val
                645                 650                 655

Leu Leu Phe Glu Thr Ala Leu Leu Ser Ser Gly Phe Ser Leu Glu Asp
            660                 665                 670

Pro Gln Thr His Ser Asn Arg Ile Tyr Arg Met Ile Lys Leu Gly Leu
        675                 680                 685

Gly Ile Asp Glu Asp Glu Val Ala Ala Glu Pro Asn Ala Ala Val
    690                 695                 700

Pro Asp Glu Ile Pro Pro Leu Glu Gly Asp Glu Asp Ala Ser Arg Met
705                 710                 715                 720

Glu Glu Val Asp

<210> SEQ ID NO 7
<211> LENGTH: 11
<212> TYPE: PRT
<213> ORGANISM: Drosophila melanogaster

<400> SEQUENCE: 7

Gln Thr Leu Val Glu Asn Glu Leu Ala Thr Arg
1               5                   10

<210> SEQ ID NO 8
<211> LENGTH: 12
<212> TYPE: PRT
<213> ORGANISM: Drosophila melanogaster

<400> SEQUENCE: 8

Ile Tyr Phe Leu Glu Glu Gly Gln Pro Gly Ala Arg
1               5                   10

<210> SEQ ID NO 9
<211> LENGTH: 15
<212> TYPE: PRT
<213> ORGANISM: Drosophila melanogaster

<400> SEQUENCE: 9

Leu Ala Asp Asp Gln Gln Asn Ser Ala Val Ile Gly Gln Leu Arg
1               5                   10                  15

<210> SEQ ID NO 10
<211> LENGTH: 14
<212> TYPE: PRT
<213> ORGANISM: Drosophila melanogaster

<400> SEQUENCE: 10

Ile Ala Gln Leu Glu Glu Gln Ile Ala Gln Lys Asp Glu Arg
1               5                   10

<210> SEQ ID NO 11
<211> LENGTH: 20
<212> TYPE: PRT
<213> ORGANISM: Drosophila melanogaster

<400> SEQUENCE: 11

Ala Ile Asn Glu Ala Leu Thr Ala Asp Leu Gln Ala Ile Gly Ser His
1               5                   10                  15

Glu Glu Glu Arg
            20
```

-continued

```
<210> SEQ ID NO 12
<211> LENGTH: 19
<212> TYPE: PRT
<213> ORGANISM: Drosophila melanogaster

<400> SEQUENCE: 12

Asp Leu Gly Ala Gln Leu Ala Asp Lys Ile Cys Glu Leu Gln Glu Ala
 1               5                  10                  15

Gln Glu Lys
```